US011918349B2

(12) United States Patent
Steil et al.

(10) Patent No.: US 11,918,349 B2
(45) Date of Patent: Mar. 5, 2024

(54) MODEL PREDICTIVE CONTROL FOR DIABETES MANAGEMENT

(71) Applicant: MEDTRONIC MINIMED, INC., Northridge, CA (US)

(72) Inventors: Garry M. Steil, Boston, MA (US); Sami S. Kanderian, Jr., Germantown, MD (US); Martin T. Cantwell, Canyon Country, CA (US); Udo Hoss, Sherman Oaks, CA (US)

(73) Assignee: MEDTRONIC MINIMED, INC., Northridge, CA (US)

( * ) Notice: Subject to any disclaimer, the term of this patent is extended or adjusted under 35 U.S.C. 154(b) by 639 days.

(21) Appl. No.: 17/084,474

(22) Filed: Oct. 29, 2020

(65) Prior Publication Data
US 2021/0038134 A1 Feb. 11, 2021

Related U.S. Application Data

(63) Continuation of application No. 16/154,997, filed on Oct. 9, 2018, now Pat. No. 10,856,786, which is a
(Continued)

(51) Int. Cl.
*A61B 5/145* (2006.01)
*A61B 5/00* (2006.01)
(Continued)

(52) U.S. Cl.
CPC ...... *A61B 5/14532* (2013.01); *A61B 5/14865* (2013.01); *A61B 5/4839* (2013.01);
(Continued)

(58) Field of Classification Search
CPC . A61B 5/14532; A61B 5/7275; A61B 5/4839; G16H 20/17; G16H 20/10; G16H 50/20; G06F 19/3468
See application file for complete search history.

(56) References Cited

U.S. PATENT DOCUMENTS 4,433,072 A 2/1984 Pusineri et al.
4,494,950 A 1/1985 Fischell
(Continued)

FOREIGN PATENT DOCUMENTS

EP 1102194 A2 5/2001
EP 1338295 A1 8/2003
(Continued)

OTHER PUBLICATIONS

Shults et al., "A Telemetry-Instrumentation System for Monitoring Multiple Subcutaneously Implanted Glucose Sensors," IEEE Trans. on Biomed. Eng., 1994, pp. 937-942, v41, n.10.
(Continued)

*Primary Examiner* — Carrie R Dorna
*Assistant Examiner* — Karen E Toth
(74) *Attorney, Agent, or Firm* — Weaver Austin Villeneuve & Sampson LLP

(57) ABSTRACT

Disclosed herein are techniques related to model predictive control. The techniques may involve generating a desired glucose trajectory that approaches a desired steady state setpoint from a current glucose value over a prediction horizon. The techniques may involve generating a plurality of insulin delivery patterns. Each insulin delivery pattern may correspond to an amount of insulin to be delivered over a control horizon. The techniques may involve generating a plurality of predicted glucose trajectories over the control horizon. Each predicted glucose may be generated based on the current glucose value and a respective insulin delivery pattern. The techniques may involve comparing the desired glucose trajectory against each predicted glucose trajectory and selecting a predicted glucose trajectory that is more similar to the desired glucose trajectory than any other predicted glucose trajectory. The techniques may involve
(Continued)

determining an insulin delivery pattern used to generate the selected predicted glucose trajectory.

20 Claims, 21 Drawing Sheets

Related U.S. Application Data continuation of application No. 11/700,666, filed on Jan. 31, 2007, now Pat. No. 10,154,804.

(51) Int. Cl.
| | |
|---|---|
| *A61B 5/1486* | (2006.01) |
| *A61B 5/1495* | (2006.01) |
| *A61K 38/28* | (2006.01) |
| *A61M 5/142* | (2006.01) |
| *A61M 5/158* | (2006.01) |
| *A61M 5/172* | (2006.01) |
| *G16H 20/10* | (2018.01) |
| *G16H 20/17* | (2018.01) |
| *G16Z 99/00* | (2019.01) |

(52) U.S. Cl.
CPC .......... *A61B 5/6849* (2013.01); *A61B 5/7275* (2013.01); *A61K 38/28* (2013.01); *A61M 5/14244* (2013.01); *A61M 5/1723* (2013.01); *C12Y 301/01003* (2013.01); *G16H 20/17* (2018.01); *G16Z 99/00* (2019.02); *A61B 5/1495* (2013.01); *A61M 2005/14208* (2013.01); *A61M 5/158* (2013.01); *A61M 2005/1581* (2013.01); *A61M 5/1582* (2013.01); *A61M 2205/3523* (2013.01); *A61M 2205/3561* (2013.01); *A61M 2205/3569* (2013.01); *G16H 20/10* (2018.01)

(56) References Cited

U.S. PATENT DOCUMENTS

| | | |
|---|---|---|
| 4,562,751 A | 1/1986 | Nason et al. |
| 4,671,288 A | 6/1987 | Gough |
| 4,678,408 A | 7/1987 | Nason et al. |
| 4,685,903 A | 8/1987 | Cable et al. |
| 4,731,726 A | 3/1988 | Allen, III |
| 4,781,798 A | 11/1988 | Gough |
| 4,871,351 A | 10/1989 | Feingold |
| 5,080,653 A | 1/1992 | Voss et al. |
| 5,097,122 A | 3/1992 | Colman et al. |
| 5,101,814 A | 4/1992 | Palti |
| 5,108,819 A | 4/1992 | Heller et al. |
| 5,165,407 A | 11/1992 | Wilson et al. |
| 5,262,035 A | 11/1993 | Gregg et al. |
| 5,262,305 A | 11/1993 | Heller et al. |
| 5,264,104 A | 11/1993 | Gregg et al. |
| 5,264,105 A | 11/1993 | Gregg et al. |
| 5,284,140 A | 2/1994 | Allen et al. |
| 5,299,571 A | 4/1994 | Mastrototaro |
| 5,320,725 A | 6/1994 | Gregg et al. |
| 5,322,063 A | 6/1994 | Allen et al. |
| 5,356,786 A | 10/1994 | Heller et al. |
| 5,370,622 A | 12/1994 | Livingston et al. |
| 5,371,687 A | 12/1994 | Holmes, II et al. |
| 5,376,070 A | 12/1994 | Purvis et al. |
| 5,390,671 A | 2/1995 | Lord et al. |
| 5,391,250 A | 2/1995 | Cheney, II et al. |
| 5,403,700 A | 4/1995 | Heller et al. |
| 5,411,647 A | 5/1995 | Johnson et al. |
| 5,466,465 A | 11/1995 | Royds et al. |
| 5,482,473 A | 1/1996 | Lord et al. |
| 5,497,772 A | 3/1996 | Schulman et al. |
| 5,543,326 A | 8/1996 | Heller et al. |
| 5,569,186 A | 10/1996 | Lord et al. |
| 5,586,553 A | 12/1996 | Halili et al. |
| 5,593,852 A | 1/1997 | Heller et al. |
| 5,660,163 A | 8/1997 | Schulman et al. |
| 5,665,065 A | 9/1997 | Colman et al. |
| 5,665,222 A | 9/1997 | Heller et al. |
| 5,750,926 A | 5/1998 | Schulman et al. |
| 5,779,665 A | 7/1998 | Mastrototaro et al. |
| 5,791,344 A | 8/1998 | Schulman et al. |
| 5,822,715 A | 10/1998 | Worthington et al. |
| 5,917,346 A | 6/1999 | Gord et al. |
| 5,965,501 A | 9/1999 | Brown |
| 5,904,708 A | 10/1999 | Goedeke |
| 5,965,380 A | 10/1999 | Heller et al. |
| 5,972,199 A | 10/1999 | Heller et al. |
| 5,999,848 A | 12/1999 | Gord et al. |
| 5,999,849 A | 12/1999 | Gord et al. |
| 6,043,437 A | 3/2000 | Schulman et al. |
| 6,081,736 A | 6/2000 | Colvin et al. |
| 6,083,710 A | 7/2000 | Heller et al. |
| 6,088,608 A | 7/2000 | Schulman et al. |
| 6,103,033 A | 8/2000 | Say et al. |
| 6,119,028 A | 9/2000 | Schulman et al. |
| 6,120,676 A | 9/2000 | Heller et al. |
| 6,121,009 A | 9/2000 | Heller et al. |
| 6,134,461 A | 10/2000 | Say et al. |
| 6,143,164 A | 11/2000 | Heller et al. |
| 6,162,611 A | 12/2000 | Heller et al. |
| 6,175,752 B1 | 1/2001 | Say et al. |
| 6,233,539 B1 | 5/2001 | Brown |
| 6,259,937 B1 | 7/2001 | Schulman et al. |
| 6,329,161 B1 | 12/2001 | Heller et al. |
| 6,352,505 B1 | 3/2002 | Bortz |
| 6,379,301 B1 | 4/2002 | Worthington et al. |
| 6,472,122 B1 | 10/2002 | Schulman et al. |
| 6,484,046 B1 | 11/2002 | Say et al. |
| 6,503,381 B1 | 1/2003 | Gotoh et al. |
| 6,514,718 B2 | 2/2003 | Heller et al. |
| 6,520,938 B1 | 2/2003 | Funderburk et al. |
| 6,544,212 B2 | 4/2003 | Galley et al. |
| 6,554,798 B1 | 4/2003 | Mann et al. |
| 6,558,320 B1 | 5/2003 | Causey et al. |
| 6,560,741 B1 | 5/2003 | Heller et al. |
| 6,565,509 B1 | 5/2003 | Say et al. |
| 6,572,586 B1 | 6/2003 | Wojcik |
| 6,579,690 B1 | 6/2003 | Bonnecaze et al. |
| 6,591,125 B1 | 7/2003 | Buse et al. |
| 6,592,745 B1 | 7/2003 | Feldman et al. |
| 6,605,200 B1 | 8/2003 | Mao et al. |
| 6,605,201 B1 | 8/2003 | Mao et al. |
| 6,607,658 B1 | 8/2003 | Heller et al. |
| 6,616,819 B1 | 9/2003 | Liamos et al. |
| 6,618,934 B1 | 9/2003 | Feldman et al. |
| 6,623,501 B2 | 9/2003 | Heller et al. |
| 6,654,625 B1 | 11/2003 | Say et al. |
| 6,671,554 B2 | 12/2003 | Gibson et al. |
| 6,676,816 B2 | 1/2004 | Mao et al. |
| 6,689,265 B2 | 2/2004 | Heller et al. |
| 6,733,461 B2 | 5/2004 | Ericson et al. |
| 6,746,582 B2 | 6/2004 | Heller et al. |
| 6,749,740 B2 | 6/2004 | Liamos et al. |
| 6,809,653 B1 | 10/2004 | Mann et al. |
| 6,881,552 B1 | 4/2005 | Heller et al. |
| 6,893,545 B2 | 5/2005 | Gotch et al. |
| 6,916,159 B2 | 7/2005 | Rush et al. |
| 6,925,393 B1 | 8/2005 | Kalatz et al. |
| 6,932,894 B2 | 8/2005 | Mao et al. |
| 6,942,518 B2 | 9/2005 | Liamos et al. |
| 7,167,818 B2 | 1/2007 | Brown |
| 8,257,300 B2 | 9/2012 | Budiman et al. |
| 10,154,804 B2 | 12/2018 | Steil et al. |
| 10,856,786 B2 | 12/2020 | Steil et al. |
| 2002/0082665 A1 | 6/2002 | Haller et al. |
| 2002/0161288 A1 | 10/2002 | Shin et al. |
| 2003/0028089 A1 | 2/2003 | Galley et al. |
| 2003/0061232 A1 | 3/2003 | Patterson |
| 2003/0061234 A1 | 3/2003 | Ali et al. |
| 2003/0078560 A1 | 4/2003 | Miller et al. |
| 2003/0088166 A1 | 5/2003 | Say et al. |
| 2003/0152823 A1 | 8/2003 | Heller et al. |

(56) References Cited

U.S. PATENT DOCUMENTS

| | | | |
|---|---|---|---|
| 2003/0168338 A1 | 8/2003 | Gao et al. | |
| 2003/0176183 A1 | 9/2003 | Drucker et al. | |
| 2003/0188427 A1 | 10/2003 | Say et al. | |
| 2003/0195404 A1 | 10/2003 | Knobbe et al. | |
| 2003/0199744 A1 | 10/2003 | Buse et al. | |
| 2003/0208113 A1* | 11/2003 | Mault | G16H 40/63 600/316 |
| 2003/0220552 A1 | 11/2003 | Reghabi et al. | |
| 2004/0034288 A1 | 2/2004 | Hennessy et al. | |
| 2004/0064133 A1 | 4/2004 | Miller et al. | |
| 2004/0064156 A1 | 4/2004 | Shah et al. | |
| 2004/0074785 A1 | 4/2004 | Holker et al. | |
| 2004/0093167 A1 | 5/2004 | Braig et al. | |
| 2004/0111017 A1 | 6/2004 | Say et al. | |
| 2005/0065760 A1 | 3/2005 | Murtfeldt et al. | |
| 2005/0197621 A1* | 9/2005 | Poulsen | G16H 50/50 702/19 |
| 2005/0214585 A1 | 9/2005 | Li et al. | |
| 2005/0272640 A1 | 12/2005 | Doyle, III et al. | |
| 2006/0031094 A1 | 2/2006 | Cohen et al. | |
| 2006/0173406 A1 | 8/2006 | Hayes et al. | |
| 2007/0078818 A1 | 4/2007 | Zivitz et al. | |
| 2007/0179434 A1 | 8/2007 | Weinert et al. | |
| 2007/0287985 A1 | 12/2007 | Estes et al. | |
| 2008/0147050 A1 | 6/2008 | Mann et al. | |
| 2008/0208113 A1* | 8/2008 | Damiano | G16H 50/50 604/67 |
| 2010/0292634 A1* | 11/2010 | Kircher, Jr. | G16H 20/13 604/66 |
| 2014/0068487 A1 | 3/2014 | Steiger et al. | |

FOREIGN PATENT DOCUMENTS

| | | |
|---|---|---|
| JP | 2001-204817 | 7/2001 |
| JP | 2001-252064 | 9/2001 |
| JP | 2001-252064 A | 9/2001 |
| JP | 2003-522558 A | 7/2003 |
| JP | 2006-510467 A | 3/2006 |
| JP | 2006-175227 | 7/2006 |
| WO | WO 96-37246 A1 | 11/1996 |
| WO | WO 00-74753 A1 | 12/2000 |
| WO | WO 02-058537 A2 | 8/2002 |
| WO | WO 2004-060455 A1 | 7/2004 |
| WO | WO 2005/061041 A1 | 7/2005 |
| WO | WO 2005-065542 A2 | 7/2005 |
| WO | WO 2006-019623 A2 | 2/2006 |
| WO | WO 2006-124716 A2 | 11/2006 |
| WO | WO 2007-053832 A2 | 5/2007 |

OTHER PUBLICATIONS

Wang et al., "Needle-Type Dual Microsensor for the Simultaneous Monitoring of Glucose and Insulin." Anal. Chem. 2001, pp. 844-847, vol. 73.

Moussey et al, "Performance of Subcutaneously Implanted Needle-Type Glucose Sensors Employing a Novel Trilayer Coating," Anal. Chem., 1993, 2072-77, vol. 65.

Bindra et al., "Design and In Vitro Studies of a Needle-Type Glucose Sensor for Subcutaneous Monitoring," Anal. Chem., 1991, pp. 1692-1696, vol. 63.

T. Deutsch, et al., "UTOPIA: A consultation system for visit-by-visit diabetes management", Medical Informatica, Oct. 1, 1996, vol. 21, No. 4, pp. 345-358, 0307-7640/96, Taylor & Francis Ltd. XP-002052428.

International Preliminary Report on Patentability, (PCT/US2007/026143) (9-pgs).

Sami Aknderian, Paul M. Rosman, Coleen Pomaro, Jennifer Booher, Jean Rider, & Garry M. Steil, "Relationship between Factors that Determine the Distribution of Insulin and Outcome Measures in Patients with Type I Diabetes Mellitus Treated with Insulin Pumps," Clinical Therapeutics/New Technology—Insulin Delivery Systems, Absender ZB MED (XP-9102948A), p. A498 (2005).

Kupper A. Wintergerst, Bruce Buckingham, Dorothee Deiss, Garry M. Steil, Martin Cantwell, Saraswa Tikache, Swati Agarwal, Darrell M. Wilson, "Glucose Control in Pediatric Intensive Care Unit (PICU) Patients Using an Insulin-Glucose Algorithm," Clinical Therapeutics/New Technology—Other Drug Delivery Systems, Absender ZB MED (XP-9102949A), p. A103, (2006).

Sami Kanderian, Mohammed F. Saad, Kerstin Rbrin, Garry M. Stei, "Modeling Glucose Profiles Obtained Using Closed Loop Insulin Delivery—Iplications for Controller Optimization," Clinical Therapeutics/New Technology—Insulin Delivery Systems, Absender ZB MED (XP-9102946A), p. A98, (2006).

Todd M. Gross, Ph.D., David Kayne, M.D., Allen King, M.D., Carla Rother, M.S. and Suzanne Juth, R.N., C.D.E., "A Bolus Calculatr Is an Effective Means of Controlling Postprandial Glycemia in Patients on Insulin Pump Theraphy" Diabetes Technology & Therapeutics, Mary Ann Liebert, Inc. (XP-09102940), pp. 365-369, (2003).

G.M. Steil, Ph.D., Bud Clark, M.A., Sami Kanderian, M.S.E., and K. Rebrin, M.D., Ph.D., "Modeling Insulin Action for Development of a Closed-Loop Artificial Pancreas," Diabetes Technology & Therapeutics, Mary Ann Liebert, Inc. (XP-009098760), pp. 94-109, (2005).

PCT International Search Report, dated Jul. 17, 2008, (PCT/US2007/026143), (6-pages).

The Effect of Intensive Treatment of Diabetes on the Development and Progression of Long-Term Cmplication in Insulin-Dependent Diabetes Mellitus, New England Journal of Medicine, vol. 329 No. 14, Sep. 30, 1993, pp. 977-986 (XP055050395).

Reach et al., "Experience with an implantable glucose sensor as a prerequisite of an artificial beta cell," Biomed. Biochim. Acta, 1984, pp. 577-584, vol. 5.

Abel et al., "A Method for Evaluating in vivo the Functional Characteristics of Glucose Sensors," Biosensors, 1986, pp. 211-220, vol. 2.

Boguslavsky et al., "Applications of redox polymers in biosensors," Solid State Ionics, 1993, pp. 189-197, vol. 60.

Geise et al., "Electropolymerized 1,3-diaminobenzene for the construction of a 1-1'-dimethylferrocene mediated glucose biosensor," Analytica Chim. Acta., 1993, pp. 467-473, v18.

Gernet et al., "A planar glucose enzyme electrode," Sensors and Actuators, 1989, pp. 537-540, vol. 17, Elsevier Sequoia, Netherlands.

Gernet et al., "Fabrication and Characterization of a Planar Electrochemical Cell and Its Applications as a Glucose Sensor," Sensors and Actuators, 1989, pp. 49-70, vol. 18.

Gorton et al., "Amperometric glucose sensors based on immobilized glucose-oxidizing enzymes and chemically modified electrodes," Analytic Chim Acta., 1991, pp. 43-54, v. 249.

Gorton et al., "Amperometric biosensors based on an apparent direct electron transfer between electrodes and immobilized peroxidases," Analyst, 1992, pp. 1235-1241, vol. 117.

Gough et al., "Two-Dimensional Enzyme Electrode Sensor for Glucose," Analytical Chemistry, 1985, pp. 2351-2357, vol. 57.

Gregg, et al., "Redox polymer films containing enzymes," J. Phys. Chem., 1991, pp. 5970-5975.

Gregg et al., "Cross-Linked Redox Gels Containing Glucose Oxidase for Amperometric Biosensor Applications," Anal. Chem., 1990, pp. 258-263, vol. 62.

Heller et al., "Electrical Wiring of Redox Enzymes," Accounts of Chemical Research, 1990, pp. 128-134, vol. 23, No. 5.

Johnson et al., "In vivo evaluation of an electroenzymatic glucose sensor implanted in subcutaneous tissue," Biosensors & Bioelectronics, 1992, pp. 709-714, vol. 7.

Jonsson, et al., "An Electrochemical Sensor for Hydrogen Peroxide Based on Peroxidase Absorbed on a Spectographic Graphite Electrode," Electroanalysts, 1989, pp. 465-468, v. 1.

Kanapieniene et al., "Miniature glucose biosensor with extended linearity," Sensors and Actuators, 1992, pp. 37-40, vol. B, No. 10.

Kawamori et al., "Perfect Normalization of Excessive Glucagon Responses to Intravenous Arginine in Human Diabetes Mellitus with . . . ," Diabetes, 1980, pp. 762-765, vol. 29.

Kimura, et al., "An immobilized Enzyme Membrane Fabrication Method using an Ink Jet Nozzle," Biosensors, 1988, pp. 41-52, vol. 4.

(56) References Cited

OTHER PUBLICATIONS

Koudelka, et al., "In-vivo Behavior of Hypodermically Implanted Microfabricated Glucose Sensors," Biosensors & Bioelectronics, 1991, pp. 31-36, vol. 6.

Mastrototaro et al., "An electroenzymatic glucose sensor fabricated on a flexible substrate," Sensors and Actuators, 1991, pp. 139-144, vol. 5.

Mastrototaro et al., "An Electroenzymatic Sensor Capable of 72 Hour Continuous Monitoring of Subcutaneous Glucose," 14th Int'l Diabetes Federation Congress, 1991.

McKean et al., "A Telemetry-Instrumentation System for Chronically Implanted Glucose and Oxygen Sensors," IEEE Transactions on Biomedical Eng., 1988, pp. 526-532, vol. 35, No. 7.

Monroe, "Novel implantable glucose sensors," ACL, 1989, pp. 8-16.

Morff et al., "Microfabrication of Reproducible, Economical, Electroenzymatic Glucose Sensors," Annual Int'l Conf. IEEE Eng. in Med. and Bio. Soc., 1990, pp. 483-484, v. 12, n.2.

Nakamato et al., "A Lift-Off Method for Patterning Enzyme-Immobilized Membranes in Multi-Biosensors," Sensors and Actuators, 1988, pp. 165-172, vol. 13.

Nishida et al., "Clinical applications of the wearable artificial endocrine pancreas with the newly designed . . . ," Path. and Treat. of NIDDM . . . , 1994, p. 353-358, No. 1057.

Shichiri et al., "An artificial endocrine pancrease—problems awaiting solutions for long term clinical applications of . . . ," Frontier Med. Biol. Eng., 1991, pp. 283-292, v.3.

Shichiri et al., "Wearable Artificial Endocrine Pancreas with Needle-Type Glucose Sensor," The Lancet, 1982, pp. 1129-1131, vol. 2 (8308).

Schichiri et al., "Telemetry Glucose Monitoring Device with Needle-Type Glucose Sensor," Diabetes Care, May-Jun. 1986, pp. 298-301, vol. 9, No. 3.

Shichiri et al., "Normalization of the Paradoxic Secretion of Glucagen in Diabetics Who Were Controlled by the Artificial Beta Cel," Diabetes, 1979, pp. 272-275, vol. 28.

Shichiri et al., "Closed-Loop Glycemic Control with a Wearable Artificial Endocrine Pancreas," Diabetes, 1984, pp. 1200-1202, vol. 33.

Shichiri et al., "In Vivo Characteristics of Needle-Type Glucose Sensor," Hormone and Metabolic Research, 1988, pp. 17-20, vol. 20.

Shichiri et al., "A Needle-Type Glucose Sensor," Life Support Systems. The Journal of the European Society for Artificial Organs, 1984, pp. 7-9, vol. 2, supplement 1.

Shichiri et al., "The Wearable Artificial Endocrine Pancreas with a Needle-Type Glucose Sensor," Acta Pediatr, Jpn, 1984, pp. 358-370, vol. 26.

Shichiri et al., "Glycaemic Control in Pancreatectomized Dogs with a Wearable Artificial Endocrine Pancrease," Diabetologica, 1983, pp. 179-184, vol. 24.

Shichiri et al., "Membrane design for extending the long-life of an implantable glucose sensor," Diab. Nutr. Metab., 1989, pp. 309-313, vol. 2.

Shichiri et al., "Molecular Recognition of Mono- and Di-Saccharides by Phenylboronic Acids in Solvent Extranction and as a Monolayer," J. Chem. Soc., 1991, pp. 1039-1041.

Tamiya et al., "Micro Glucose Sensors Using Electron Mediators Immobilized on a Polpyrrole-Modified Electrode," Sensors and Actuators, 1989, p. 297-307, v. 18.

Tsukagoshi et al., "Specific Complexation with Mono- and Disaccharides That Can Be Detected By Circular Dichroism," J. Org. Chem., 1991, pp. 4089-4091, vol. 56.

Urban, et al., "Miniaturized multi-enzyme biosensors integrated with pH sensors on flexible polymer carriers . . . ," Biosensors & Bioelectronics, 1992, pp. 733-739, vol. 7.

Urban et al., "Miniaturized thin-film biosensors using covalently immobilized glucose oxidase," Biosensors & Bioelectronics, 1991, p. 555-62, vol. 6.

Velho et al., "In vivo calibration of a subcutaneous glucose sensor for determination of subcutaneous glucose kinetics," Diab. Nutr. Metab., 1988 pp. 227-233, v. 3.

Yokoyama et al., "Integrated Blosensor for Glucose and Galactose," Analytica Chimica Acta., 1989, pp. 137-142, vol. 218.

Nishida et al., "Development of a ferrocene-mediated needle-type glucose sensor . . . ," Medical Process Through Technology, 1995, pp. 91-103, vol. 21.

Koudelka et al., "Planar Amperometric Enzyme-Based Glucose Microelectrode," Sensors and Actuators, 1989, pp. 157-165, vol. 18.

Yamasaki et al., "Direct measurement of whole blood glucose by a needle-type sensor," Clinical Chimica Acta., 1989, pp. 93-98, vol. 93.

Sternberg et al., "Study and Development of Multilayer Needle-type Enzyme-based Glucose Microsensors," Biosensors, 1988, pp. 27-40, vol. 4.

Shaw et al., "In vitro testing of a simply constructed, highly stable glucose sensor suitable for implantation . . . ," Biosensors & Bioelectronics, 1991, pp. 401-406, vol. 6.

Poitout et al., "A glucose monitoring system for on line estimation in man of blood glucose concentration using a miniaturized . . . ," Diabetologia, 1993, pp. 658-663, vol. 36.

Hashigushi et al., "Development of a Miniaturized Glucose Monitoring System by Combining a Needle-Type Glucose Sensor . . . ," Diabetes Care, 1994, pp. 387-389, v. 17, n. 5.

Jobst et al., "Thin-Film Microbiosensors for Glucose-Lactate Monitoring," Anal. Chem., 1996, p. 3173-79, vol. 68.

\* cited by examiner

| COMPONENTS | ALTERNATIVE, FIG. 8(a) | | PREFERRED EMBODIMENT, FIG. 8(b) | | ALTERNATIVE, FIG. 8(c) | | ALTERNATIVE, FIG. 8(d) | | |
|---|---|---|---|---|---|---|---|---|---|
| | TELEMETERED CHARACTERISTIC MONITOR TRANSMITTER | INFUSION PUMP | TELEMETERED CHARACTERISTIC MONITOR TRANSMITTER | INFUSION PUMP | TELEMETERED CHARACTERISTIC MONITOR TRANSMITTER | INFUSION PUMP | TELEMETERED CHARACTERISTIC MONITOR TRANSMITTER | SUPPLEMENTAL DEVICE | SUPPLEMENTAL INFUSION PUMP |
| PRE-FILTERS | | X | X | | X | | X | | |
| FILTERS | | X | X | | | X | | X | |
| CALIBRATOR | | X | | | | X | | X | |
| CONTROLLER | | X | | X | | X | | | X |

FIG. 9

MODEL PREDICTIVE CONTROL FOR DIABETES MANAGEMENT

RELATED APPLICATION DATA

This application is a continuation of U.S. patent application Ser. No. 16/154,997, filed Oct. 9, 2018, now U.S. Pat. No. 10,856,786, issued on Dec. 8, 2020, which is a continuation of U.S. patent application Ser. No. 11/700,666, filed Jan. 31, 2007, now U.S. Pat. No. 10,154,804, issued on Dec. 18, 2018. Each of the foregoing applications is hereby incorporated herein by reference in its entirety.

FIELD

This invention relates generally to model predictive control and supervision, and more specifically, to model predictive control for diabetes management.

BACKGROUND

The pancreas of a normal healthy person produces and releases insulin into the blood stream in response to elevated blood plasma glucose levels. Beta cells (β-cells), which reside in the pancreas, produce and secrete the insulin into the blood stream, as it is needed. If β-cells become incapacitated or die, a condition known as Type I diabetes mellitus (or in some cases if β-cells produce insufficient quantities of insulin, Type II diabetes), then insulin must be provided to the body from another source.

Traditionally, since insulin cannot be taken orally, insulin has been injected with a syringe. More recently, the use of infusion pump therapy has been increasing, especially for delivering insulin for diabetics. For example, external infusion pumps are worn on a belt, in a pocket, or the like, and deliver insulin into the body via an infusion tube with a percutaneous needle or a cannula placed in the subcutaneous tissue. As of 1995, less than 5% of Type I diabetics in the United States were using infusion pump therapy. More recently, over 7% of the more than 900,000 Type I diabetics in the U.S. are using infusion pump therapy. Also, the percentage of Type I diabetics who use an infusion pump is growing at an absolute rate of over 2% each year. Moreover, the number of Type I diabetics is growing at 3% or more per year. In addition, growing numbers of insulin-using Type II diabetics are also using infusion pumps. Physicians have recognized that continuous infusion provides greater control of a diabetic's condition, and are also increasingly prescribing it for patients.

Infusion pump devices and systems are relatively well-known in the medical arts for use in delivering or dispensing a prescribed medication, such as insulin, to a patient. In one form, such devices comprise a relatively compact pump housing adapted to receive a syringe or reservoir carrying a prescribed medication for administration to the patient through infusion tubing and an associated catheter or infusion set. Programmable controls can operate the infusion pump continuously or at periodic intervals to obtain a closely controlled and accurate delivery of the medication over an extended period of time. Such infusion pumps are used to administer insulin and other medications, with exemplary pump constructions being shown and described in U.S. Pat. Nos. 4,562,751; 4,678,408; 4,685,903; 5,080,653; and 5,097,122, which are incorporated by reference herein.

There is a baseline insulin need for each body which, in diabetic individuals, may generally be maintained by administration of a basal amount of insulin to the patient on a continual, or continuous, basis using infusion pumps. However, when additional glucose (i.e., beyond the basal level) appears in a diabetic individual's body, such as, for example, when the individual consumes a meal, the amount and timing of the insulin to be administered must be determined so as to adequately account for the additional glucose while, at the same time, avoiding infusion of too much insulin. Typically, a bolus amount of insulin is administered to compensate for meals (i.e., meal bolus). It is common for diabetics to determine the amount of insulin that they may need to cover an anticipated meal based on carbohydrate content of the meal.

Although the administration of basal and bolus amounts of insulin from an infusion pump provides a diabetic individual reasonable control of his/her blood glucose levels, there still exists a need to better provide control for the administration of insulin to more closely resemble the body's insulin response, and to avoid overdoses of insulin.

SUMMARY

Disclosed herein are techniques related to model predictive control. The techniques may be practiced using a processor-implemented method; a system comprising one or more processors and one or more processor-readable storage media; and/or one or more non-transitory processor-readable storage media.

In some embodiments, the techniques may involve generating a desired glucose trajectory that approaches a desired steady state setpoint from a current glucose value over a prediction horizon. The techniques may involve generating a plurality of insulin delivery patterns. Each insulin delivery pattern may correspond to an amount of insulin to be delivered over a control horizon. The techniques may involve generating a plurality of predicted glucose trajectories over the control horizon. Each predicted glucose may be generated based on the current glucose value and a respective insulin delivery pattern. The techniques may involve comparing the desired glucose trajectory against each predicted glucose trajectory and selecting a predicted glucose trajectory that is more similar to the desired glucose trajectory than any other predicted glucose trajectory. The techniques may involve determining an insulin delivery pattern used to generate the selected predicted glucose trajectory.

BRIEF DESCRIPTION OF THE DRAWINGS

A detailed description of embodiments of the invention will be made with reference to the accompanying drawings, wherein like numerals designate corresponding parts in the several figures.

FIG. 9 is a table listing the devices of FIGS. 8A-8D and their components.

DETAILED DESCRIPTION

Figure 1:
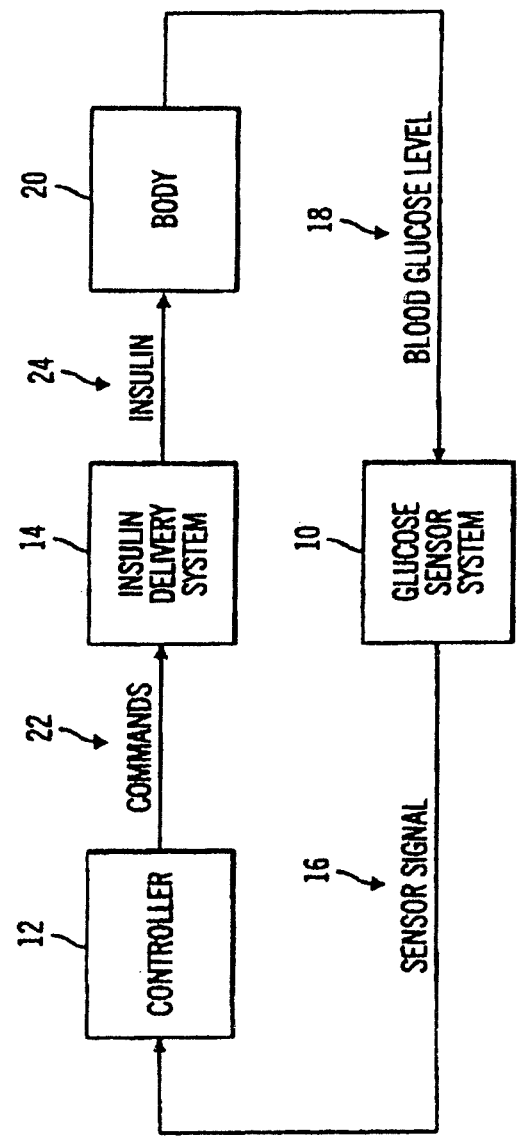
FIG. 1 is a block diagram of a closed loop glucose control system in accordance with an embodiment of the present invention.

In the following description, reference is made to the accompanying drawings which form a part hereof and which illustrate several embodiments of the present inventions. It is understood that other embodiments may be utilized and structural and operational changes may be made without departing from the scope of the present inventions.

It is also noted that the present invention is described below with reference to flowchart illustrations of methods, apparatus, and/or computer program products. It will be understood that each block of the flowchart illustrations, and combinations of blocks in the flowchart illustrations, can be implemented by computer program instructions. These computer program instructions may be loaded onto a computer or other programmable data processing apparatus (including, e.g., the controller 12), such that the instructions which execute on the computer or other programmable data processing apparatus create instructions for implementing the functions specified in the flowchart block or blocks. These computer program instructions may also be stored in a computer-readable memory that can direct a computer or other programmable data processing apparatus to function in a particular manner, such that the instructions stored in the computer-readable memory produce an article of manufacture including instructions which implement the function specified in the flowchart block or blocks. The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide steps for implementing the functions specified in the flowchart block or blocks.

As shown in the drawings for purposes of illustration, the invention may be embodied in a closed loop or semi-closed loop diabetes-management system having a sensor, a controller, and an infusion system for regulating the rate of fluid infusion into a body of a user based on user-specific input variables and feedback from an analyte concentration measurement taken from the user's body. In particular embodiments, the invention is embodied in a control system for regulating the rate of insulin infusion into the body of a user based on a glucose concentration measurement taken from the body. In preferred embodiments, the system is designed to model a pancreatic beta cell ($\beta$-cell). In other words, the system controls an infusion device to release insulin into a body of a user in a similar concentration profile as would be created by fully functioning human $\beta$-cells when responding to changes in blood glucose concentrations in the body.

Thus, the system simulates the body's natural insulin response to blood glucose levels and not only makes efficient use of insulin, but also accounts for other bodily functions as well since insulin has both metabolic and mitogenic effects. However, the algorithms must model the $\beta$-cells closely, since algorithms that are designed to minimize glucose excursions in the body, without regard for how much insulin is delivered, may cause excessive weight gain, hypertension, and atherosclerosis. Similarly, algorithms that are designed to minimize glucose excursions in the body without regard for the time period over which the glucose excursion may occur, or the time period over which the insulin is delivered and/or the insulin-delivery pattern, may lead to hypoglycemia, thereby causing dizziness, or, in severe cases, death.

In preferred embodiments of the present invention, the system is intended to emulate the in vivo insulin secretion pattern and to adjust this pattern consistent with the in vivo β-cell adaptation experienced by normal healthy individuals. The in vivo β-cell response in subjects with normal glucose tolerance (NGT), with widely varying insulin sensitivity ($S_I$), is the optimal insulin response for the maintenance of glucose homeostasis.

For example, one way to neutralize glucose appearance due to consumption of a meal is to deliver insulin in a combination mode, where the amount of insulin to be delivered is divided (e.g., 50%-50%) between a bolus and an extended basal amount over a period of time. Nevertheless, the form of insulin delivery that is most favored by diabetics, even amongst those who use pumps, is that of a single bolus of short-acting insulin, which is achieved by either injection or an infusion pump of the type discussed above. In general, this tendency to favor the single-bolus approach of delivery may be attributed to the average diabetic patient's limited understanding of how various bolus types, taken with various meals, affect their post-prandial glucose profiles.

However, it is known that the carbohydrates of different foods manifest themselves as glucose in the blood plasma at different rates. As such, it would be advantageous to account to some degree for this rate of appearance, rather than simply the total amount of carbohydrates. Put another way, a slice of pizza, a bowl of salad, and a glass of orange juice may contain the same amount of total carbohydrates (e.g., 50 grams). However, whereas the carbohydrates of the glass of orange juice may appear in the plasma within 15 minutes of consumption (i.e., where 15 minutes represents the peak of the appearance rate), the carbohydrates from consuming the slice of pizza may take upwards of 180-200 minutes to appear. Therefore, treating both meals simply by administering a single bolus that covers for a 50-carbohydrate meal, while effective, would provide a less-than-optimal response.

Similarly, in deciding whether to administer additional insulin (e.g., a corrective bolus), diabetic individuals—or in a closed-loop system, the controller—normally consider insulin on board, which may be defined as the total amount of insulin existing within the body. Insulin on board, however, is less useful as a strategic tool than the plasma insulin concentration because, by definition, for any individual, his/her insulin on board is always decreasing. However, at any given point in time after administration of a bolus, the concentration of insulin in the plasma may be either increasing or decreasing.

And knowing whether the insulin concentration is increasing or decreasing would allow the patient to make a more informed decision about if, when, and how much additional insulin is needed. For example, without this information, a patient who has recently administered a bolus of insulin, upon learning that his glucose level is still high, may be apt to administer an additional bolus. However, if a patient knows that his insulin concentration is increasing, he may realize that the initial insulin has not yet taken its full effect, and that he should wait before administering an additional bolus. Thus, while insulin on board is informative, it does not convey as much information as insulin concentration. To this end, a plasma insulin profile would provide to the patient not only the amount of insulin on board, but also an indication as to whether the patient's insulin concentration is rising or falling.

In the same vein, it is generally known that the in vivo β-cell response to changes in glucose is characterized by "first" and "second" phase insulin responses. Thus far, this biphasic insulin response has been modeled using components of a proportional, plus integral, plus derivative (PID) controller. Depending on the application, a PID controller may prove advantageous since PID algorithms are generally known to be stable for a wide variety of non-medical dynamic systems, and PID algorithms have been found to be stable over widely varying disturbances and changes in system dynamics.

Nevertheless, existing diabetes-management systems, such as those that employ PID controllers, consider historical data and the current state of the body, only. As such, they do not adequately account for delays in the insulin-delivery/ glucose concentration process. This is significant because, for a user who has recently consumed a meal, and has also had a bolus of insulin administered to cover the meal, the PID controller of an existing system that is continually monitoring the user's glucose concentration level may find a relatively high glucose level even after the bolus has been delivered. The PID controller may then determine that an additional bolus should be administered. In this way, a PID controller may suggest several consecutive infusions, without considering the long-range impact (e.g., hypoglycemia) of the combination of all of the delivered boluses once they have collectively taken their maximum effect in the user's body. There is therefore a need for a diabetes-management system, with an adaptive controller, that enables optimization of insulin delivery into the body of a user while, at the same time, allowing continuous monitoring of the operation of the diabetes-management system.

In light of the above-noted need, a preferred closed-loop embodiment of the invention is practiced with a glucose sensor system 10, a controller 12, and an insulin delivery system 14, as shown in FIG. 1. The glucose sensor system 10 generates a sensor signal 16 representative of blood glucose levels 18 in the body 20, and provides the sensor signal 16 to the controller 12. The controller 12 receives the sensor signal 16 and generates commands 22 that are communicated to the insulin delivery system 14. The insulin delivery system 14 receives the commands 22 and infuses insulin 24 into the body 20 in response to the commands 22.

Generally, the glucose sensor system 10 includes a glucose sensor, sensor electrical components to provide power to the sensor and generate the sensor signal 16, a sensor communication system to carry the sensor signal 16 to the controller 12, and a sensor system housing for the electrical components and the sensor communication system.

Typically, the controller 12 includes controller electrical components and software to generate commands for the insulin delivery system 14 based on the sensor signal 16, and a controller communication system to receive the sensor signal 16 and carry commands to the insulin delivery system 14.

Generally, the insulin delivery system 14 includes an infusion device and an infusion tube to infuse insulin 24 into the body 20. In particular embodiments, the infusion device includes infusion electrical components to activate an infusion motor according to the commands 22, an infusion communication system to receive the commands 22 from the controller 12, and an infusion device housing to hold the infusion device.

In preferred embodiments, the controller 12 is housed in the infusion device housing and the infusion communication system is an electrical trace or a wire that carries the commands 22 from the controller 12 to the infusion device.

In alternative embodiments, the controller 12 is housed in the sensor system housing and the sensor communication system is an electrical trace or a wire that carries the sensor signal 16 from the sensor electrical components to the controller electrical components. In other alternative embodiments, the controller 12 has its own housing or is included in a supplemental device. In another alternative embodiment, the controller is located with the infusion device and the sensor system all within one housing. In further alternative embodiments, the sensor, controller, and/or infusion communication systems may utilize a cable, a wire, fiber optic lines, RF, IR, or ultrasonic transmitters and receivers, or the like instead of the electrical traces. In yet other alternative embodiments, one or more of the components and/or housing units mentioned above may include a display for displaying, e.g., sensor readings, insulin-delivery rates/patterns, glucose concentration profiles, insulin concentration profiles, audio/visual/sensory warnings to the user, etc.

In a semi-closed loop embodiment, the sensor signal 16 may be provided directly to the user, who then determines, based on the blood glucose level 18, the amount and timing of insulin delivery to the body, and instructs the controller 12 and/or the insulin delivery system 14 accordingly. Alternatively, in a more preferred semi-closed loop embodiment, the controller 12 makes the above determination based on the sensor signal 16 and generates recommendations that are provided directly to the user, who must then expressly confirm them. Once the controller 12 receives the user's confirmation, it generates commands 22 that are communicated to the insulin delivery system 14 for administering insulin 24 to the user's body.

In the preferred semi-closed loop embodiment, the controller 12 includes controller electrical components and software to make calculations and generate recommendations for the user based on the sensor signal 16, and a controller communication system to receive the sensor signal 16, generate recommendations to the user, and carry commands to the insulin delivery system 14.

Figure 2:
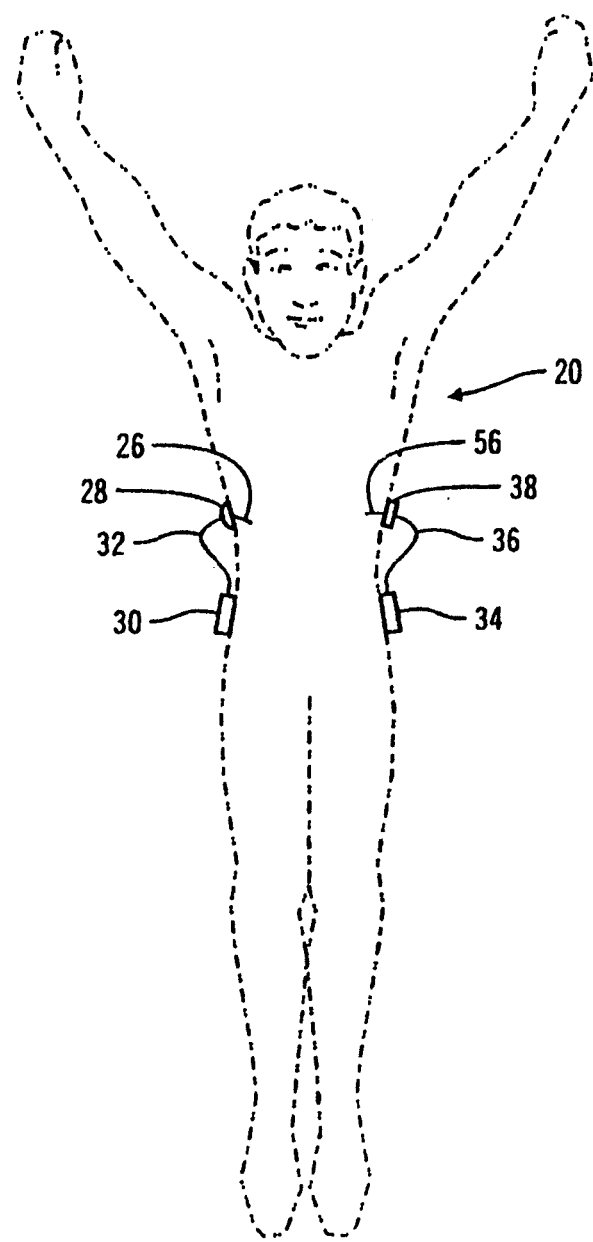
FIG. 2 is a front view of closed loop hardware located on a body in accordance with an embodiment of the present invention.
Figures 3A, 3B:
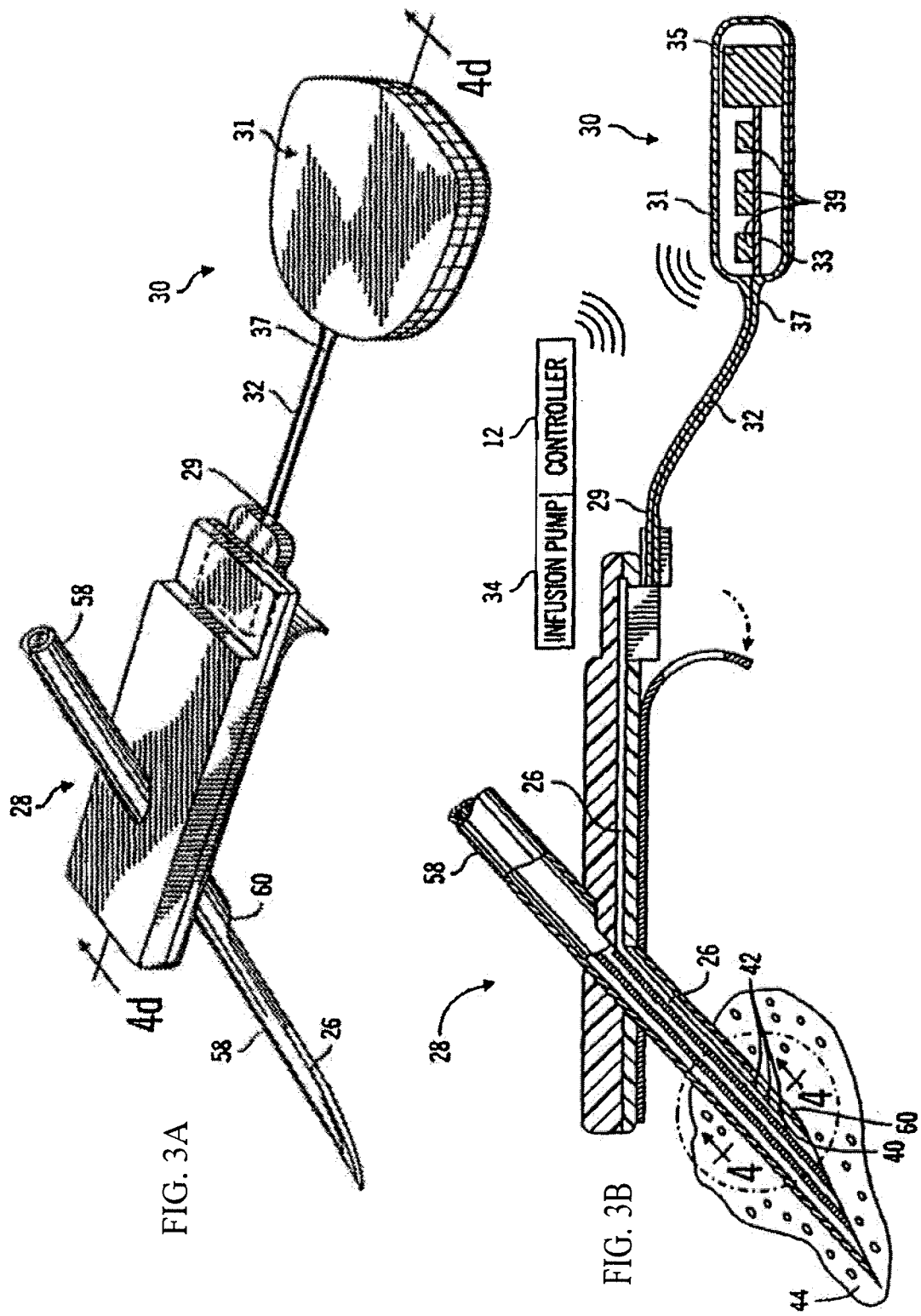
FIG. 3A is a perspective view of a glucose sensor system for use in an embodiment of the present invention.
FIG. 3B is a side cross-sectional view of the glucose sensor system of FIG. 3A.
Figure 3C:
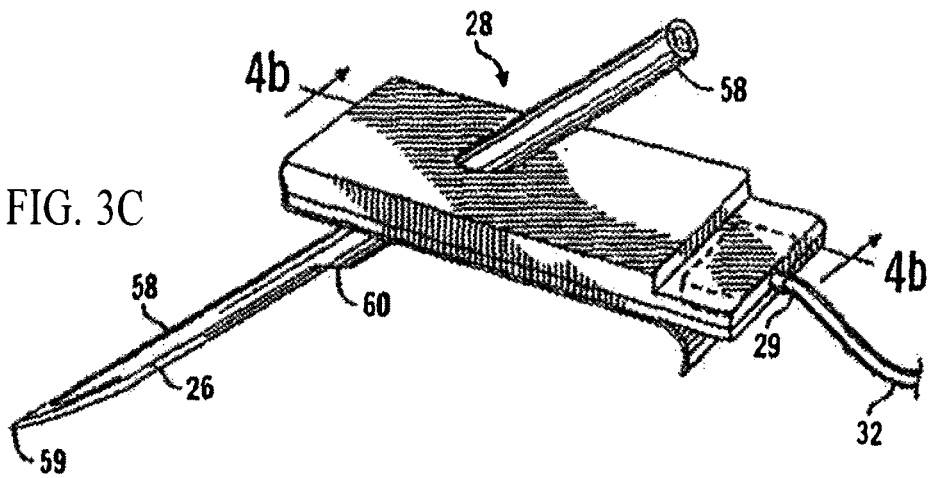
FIG. 3C is a perspective view of a sensor set of the glucose sensor system of FIG. 3A for use in an embodiment of the present invention.
Figure 3D:
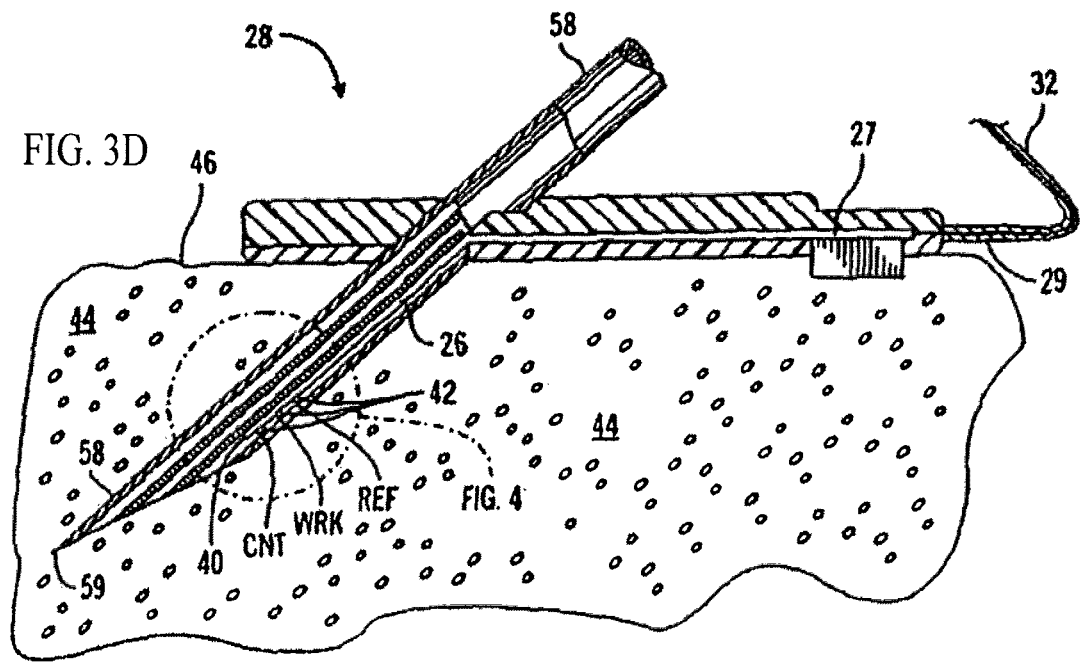
FIG. 3D is a side cross-sectional view of the sensor set of FIG. 3C.
Figure 4:
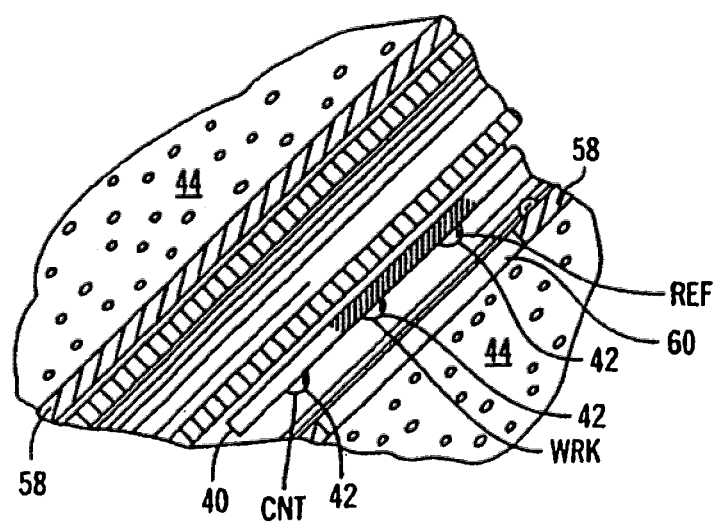
FIG. 4 is a cross sectional view of a sensing end of the sensor of FIG. 3D.

As shown in FIG. 2, in preferred embodiments, the present invention may be practiced with a diabetes-management system comprising a sensor 26, a sensor set 28, a telemetered characteristic monitor 30, a sensor cable 32, an infusion device 34, an infusion tube 36, and an infusion set 38, all worn on the body 20 of a user. The telemetered characteristic monitor 30 includes a monitor housing 31 that supports a printed circuit board 33, batteries 35, antenna (not shown), and a sensor cable connector (not shown), as seen in FIGS. 3A and 3B. A sensing end 40 of the sensor 26 has exposed electrodes 42 and is inserted through skin 46 into a subcutaneous tissue 44 of a user's body 20, as shown in FIGS. 3D and 4. The electrodes 42 are in contact with interstitial fluid (ISF) that is present throughout the subcutaneous tissue 44. The sensor 26 is held in place by the sensor set 28, which is adhesively secured to the user's skin 46, as shown in FIG. 3C and FIG. 3D. The sensor set 28 provides for a connector end 27 of the sensor 26 to connect to a first end 29 of the sensor cable 32. A second end 37 of the sensor cable 32 connects to the monitor housing 31. The batteries 35 included in the monitor housing 31 provide power for the sensor 26 and electrical components 39 on the printed circuit board 33. The electrical components 39 sample the sensor signal 16 and store digital sensor values (Dsig) in a memory and then periodically transmit the digital sensor values Dsig from the memory to the controller 12, which is included in the infusion device.

Figure 5:
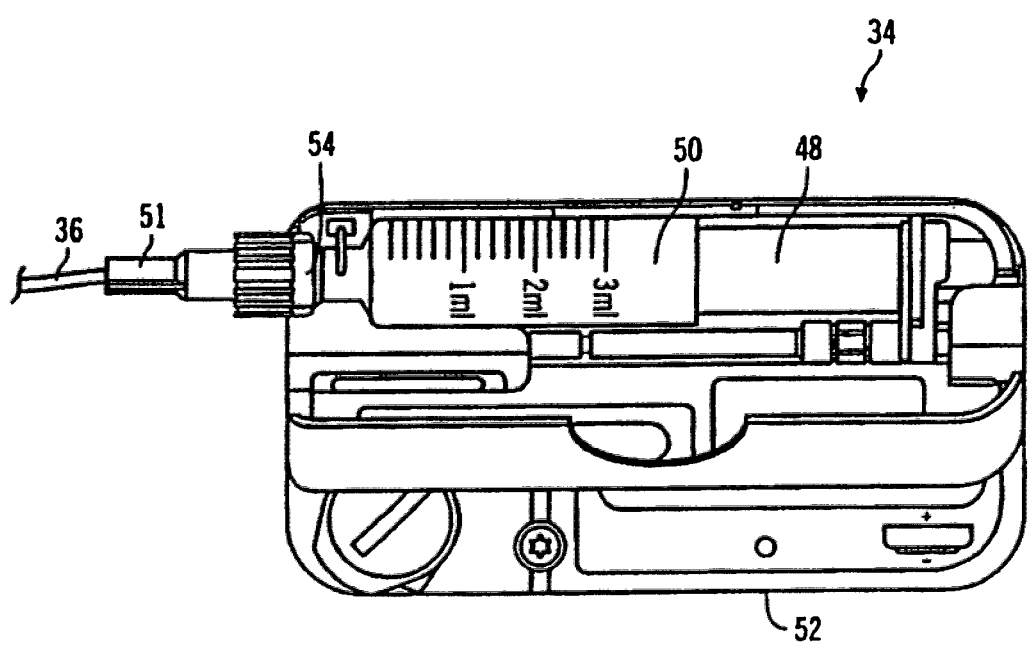
FIG. 5 is a top view of an infusion device with a reservoir door in the open position, for use in an embodiment of the present invention.
Figure 6:
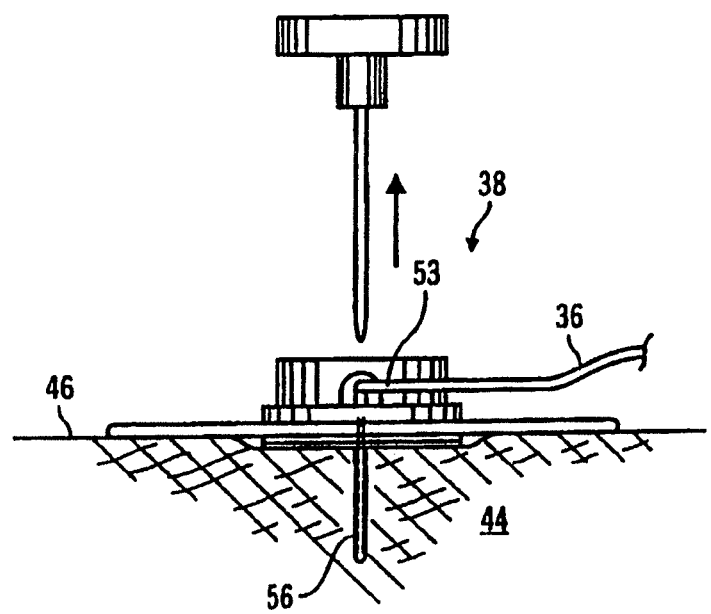
FIG. 6 is a side view of an infusion set with the insertion needle pulled out, for use in an embodiment of the present invention.

The controller 12 processes the digital sensor values Dsig and generates commands 22 for the infusion device 34. Preferably, the infusion device 34 responds to the commands 22 and actuates a plunger 48 that forces insulin 24 out of a reservoir 50 located inside the infusion device 34, as shown in FIG. 5. In particular embodiments, a connector tip 54 of the reservoir 50 extends through the infusion device housing 52 and a first end 51 of the infusion tube 36 is attached to the connector tip 54. A second end 53 of the infusion tube 36 connects to the infusion set 38. Insulin 24 is forced through the infusion tube 36 into the infusion set 38 and into the body 20. The infusion set 38 is adhesively attached to the user's skin 46, as shown in FIG. 6. As part of the infusion set 38, a cannula 56 extends through the skin 46 and terminates in the subcutaneous tissue 44 completing fluid communication between the reservoir 50 and the subcutaneous tissue 44 of the user's body 20.

In alternative embodiments, the system components may be combined in a smaller or greater number of devices and/or the functions of each device may be allocated differently to suit the needs of the user.

Figure 8:
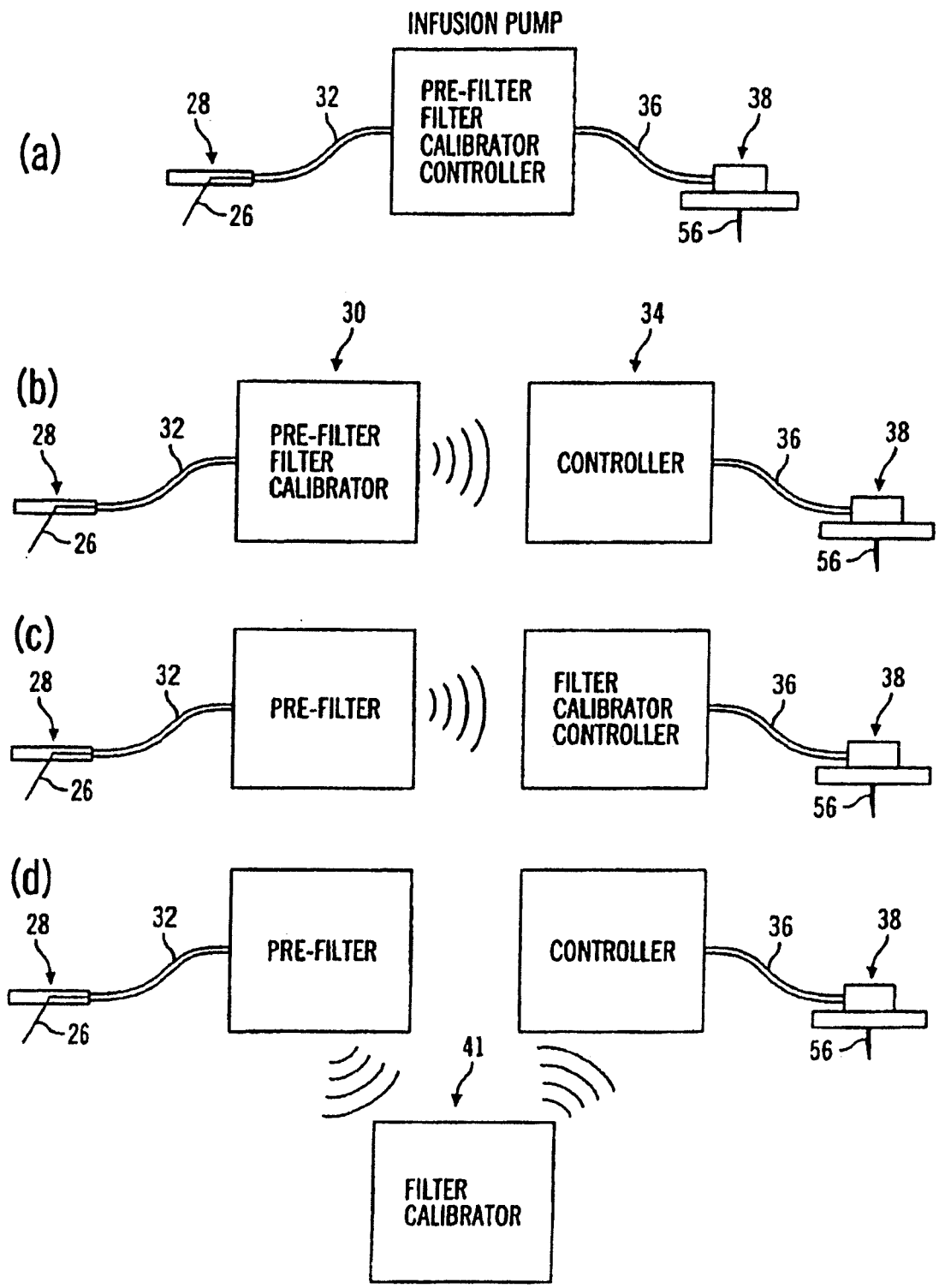
FIG. 8A is a diagram of a single device and its components in accordance with an embodiment of the present invention.
FIG. 8B is a diagram of two devices and their components in accordance with an embodiment of the present invention.
FIG. 8C is another diagram of two devices and their components in accordance with an embodiment of the present invention.
FIG. 8D is a diagram of three devices and their components in accordance with an embodiment of the present invention.

In embodiments of the invention, before it is provided as an input to the controller 12, the sensor signal 16 is generally subjected to signal conditioning such as pre-filtering, filtering, calibrating, or the like. Components such as a pre-filter, one or more filters, a calibrator and the controller 12 may be split up or physically located together, and may be included with a telemetered characteristic monitor transmitter 30, the infusion device 34, or a supplemental device. In preferred embodiments, the pre-filter, filters, and the calibrator are included as part of the telemetered characteristic monitor transmitter 30, and the controller 12 is included with the infusion device 34, as shown in FIG. 8B. In alternative embodiments, the pre-filter is included with the telemetered characteristic monitor transmitter 30 and the filter and calibrator are included with the controller 12 in the infusion device, as shown in FIG. 8C. In other alternative embodiments, the pre-filter may be included with the telemetered characteristic monitor transmitter 30, while the filter and calibrator are included in the supplemental device 41, and the controller is included in the infusion device, as shown in FIG. 8D. To illustrate the various embodiments in another way, FIG. 9 shows a table of the groupings of components (pre-filter, filters, calibrator, and controller) in various devices (telemetered characteristic monitor transmitter, supplemental device, and infusion device) from FIGS. 8A-8D. In other alternative embodiments, a supplemental device contains some (or all) of the components.

In preferred embodiments, the sensor system generates a message that includes information based on the sensor signal such as digital sensor values, pre-filtered digital sensor values, filtered digital sensor values, calibrated digital sensor values, commands, or the like. The message may include other types of information as well such as a serial number, an ID code, a check value, values for other sensed parameters, diagnostic signals, other signals, or the like. In particular embodiments, the digital sensor values Dsig may be filtered in the telemetered characteristic monitor transmitter 30, and then the filtered digital sensor values may be included in the message sent to the infusion device 34 where the filtered digital sensor values are calibrated and used in the controller. In other embodiments, the digital sensor values Dsig may be filtered and calibrated before being sent to the controller 12 in the infusion device 34. Alternatively, the digital sensor values Dsig may be filtered, and calibrated and used in the controller to generate commands 22 that are then sent from the telemetered characteristic monitor transmitter 30 to the infusion device 34.

In further embodiments, additional optional components, such as a post-calibration filter, a display, a recorder, and a blood glucose meter may be included in the devices with any of the other components or they may stand-alone. Generally, if a blood glucose meter is built into one of the devices, it will be co-located in the device that contains the calibrator. In alternative embodiments, one or more of the components are not used. Also, as noted, in semi-closed loop embodiments, signals, messages, commands, etc. may be sent to, or displayed for, the user, who then completes the loop by actively providing instructions to the controller and/or the infusion device.

In preferred embodiments, RF telemetry is used to communicate between devices, such as the telemetered characteristic monitor transmitter 30 and the infusion device 34, which contain groups of components. In alternative embodiments, other communication mediums may be employed between devices such as wires, cables, IR signals, laser signals, fiber optics, ultrasonic signals, or the like.

In preferred embodiments, after filtering, the digital sensor values Dsig are calibrated with respect to one or more glucose reference values. The glucose reference values are entered into the calibrator and compared to the digital sensor values Dsig. The calibrator applies a calibration algorithm to convert the digital sensor values Dsig, which are typically in counts into blood glucose values. In particular embodiments, the calibration method is of the type described in U.S. patent application Ser. No. 09/511,580, filed on Feb. 23, 2000, entitled "GLUCOSE MONITOR CALIBRATION METHODS", which is incorporated by reference herein. In particular embodiments, the calibrator is included as part of the infusion device 34 and the glucose reference values are entered by the user into the infusion device 34. In other embodiments, the glucose reference values are entered into the telemetered characteristic monitor transmitter 30 and the calibrator calibrates the digital sensor values Dsig and transmits calibrated digital sensor values to the infusion device 34. In further embodiments, the glucose reference values are entered into a supplemental device where the calibration is executed. In alternative embodiments, a blood glucose meter is in communication with the infusion device 34, telemetered characteristic monitor transmitter 30, or supplemental device so that glucose reference values may be transmitted directly into the device that the blood glucose meter is in communication with. In additional alternative embodiments, the blood glucose meter is part of the infusion device 34, telemetered characteristic monitor transmitter 30, or supplemental device such as that shown in U.S. patent application Ser. No. 09/334,996, filed on Jun. 17, 1999, entitled "CHARACTERISTIC MONITOR WITH A CHARACTERISTIC METER AND METHOD OF USING THE SAME", which is incorporated by reference herein.

In preferred embodiments, to obtain blood glucose reference values, one or more blood samples are extracted from the body 20, and a common, over-the-counter, blood glucose meter is used to measure the blood plasma glucose concentration of the samples. Then a digital sensor value Dsig is compared to the blood glucose measurement from the meter and a mathematical correction is applied to convert the digital sensor values Dsig to blood glucose values. In alternative embodiments, a solution of a known glucose concentration is introduced into the subcutaneous tissue surrounding the sensor 26 by using methods and apparatus such as described in U.S. patent application Ser. No. 09/395,530, filed on Sep. 14, 1999, entitled "METHOD AND KIT FOR SUPPLYING A FLUID TO A SUBCUTANEOUS PLACEMENT SITE", which is incorporated by reference herein, or by using injection, infusion, jet pressure, introduction through a lumen, or the like. A digital sensor value Dsig is collected while the sensor 26 is bathed in the solution of known glucose concentration. A mathematical formula such as a factor, an offset, an equation, or the like, is derived to convert the digital sensor value Dsig to the known glucose concentration. The mathematical formula is then applied to subsequent digital sensors values Dsig to obtain blood glucose values. In alternative embodiments, the sensors are calibrated before they are used in the body or do not require calibration at all.

Thus, the sensor system provides the glucose measurements used by the controller. The sensor system includes a sensor, a sensor set to hold the sensor if needed, a telemetered characteristic monitor transmitter, and a cable if needed to carry power and/or the sensor signal between the sensor and the telemetered characteristic monitor transmitter.

In preferred embodiments, the glucose sensor system 10 includes a thin film electrochemical sensor such as the type disclosed in U.S. Pat. No. 5,391,250, entitled "METHOD OF FABRICATING THIN FILM SENSORS"; U.S. patent application Ser. No. 09/502,204, filed on Feb. 10, 2000, entitled "IMPROVED ANALYTE SENSOR AND METHOD OF MAKING THE SAME"; or other typical thin film sensors such as described in commonly assigned U.S. Pat. Nos. 5,390,671; 5,482,473; and 5,586,553 which are incorporated by reference herein. See also U.S. Pat. No. 5,299,571.

The glucose sensor system 10 also includes a sensor set 28 to support the sensor 26 such as described in U.S. Pat. No. 5,586,553, entitled "TRANSCUTANEOUS SENSOR INSERTION SET" (published as PCT Application WO 96/25088); and U.S. Pat. No. 5,954,643, entitled "INSERTION SET FOR A TRANSCUTANEOUS SENSOR" (published as PCT Application WO 98/56293); and U.S. Pat. No. 5,951,521, entitled "A SUBCUTANEOUS IMPLANTABLE SENSOR SET HAVING THE CAPABILITY TO REMOVE OR DELIVER FLUIDS TO AN INSERTION SITE", which are incorporated by reference herein.

In preferred embodiments, the sensor 26 is inserted through the user's skin 46 using an insertion needle 58, which is removed and disposed of once the sensor is positioned in the subcutaneous tissue 44. The insertion needle 58 has a sharpened tip 59 and an open slot 60 to hold the sensor during insertion into the skin 46, as shown in FIGS. 3C and 3D and FIG. 4. Further description of the needle 58 and the sensor set 28 are found in U.S. Pat. No. 5,586,553, entitled "TRANSCUTANEOUS SENSOR INSERTION SET" (published as PCT Application WO 96/25088); and U.S. Pat. No. 5,954,643, entitled "INSERTION SET FOR A TRANSCUTANEOUS SENSOR" (published as PCT Application WO 98/5629), which are incorporated by reference herein.

Figure 7:
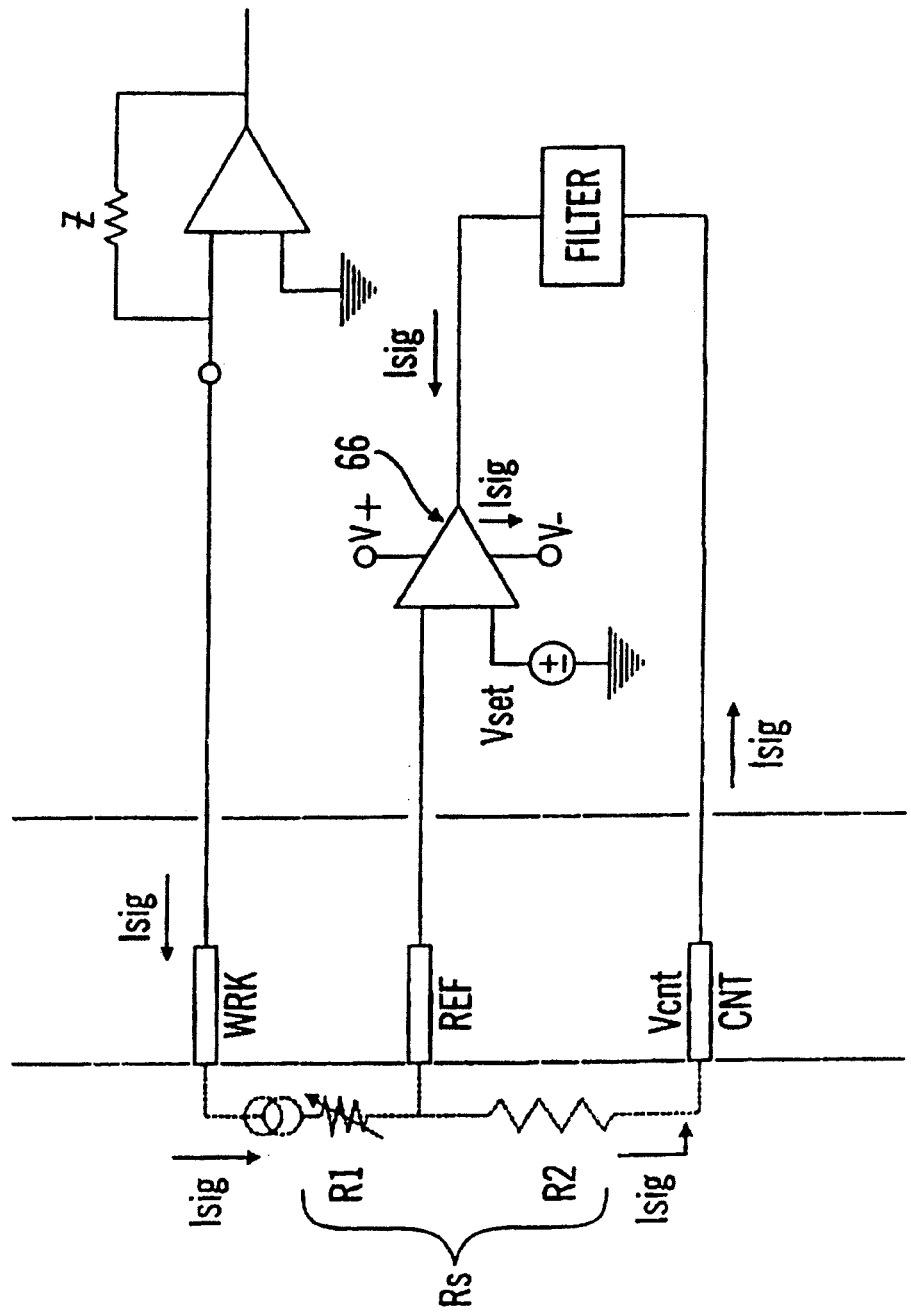
FIG. 7 is a circuit diagram of a sensor and its power supply in accordance with an embodiment of the present invention.

In preferred embodiments, the sensor 26 has three electrodes 42 that are exposed to the interstitial fluid (ISF) in the subcutaneous tissue 44 as shown in FIGS. 3D and 4. A working electrode WRK, a reference electrode REF, and a counter electrode CNT are used to form a circuit, as shown in FIG. 7. When an appropriate voltage is supplied across the working electrode WRK and the reference electrode REF, the ISF provides impedance (R1 and R2) between the electrodes 42. And an analog current signal Isig flows from the working electrode WRK through the body (R1 and R2, which sum to Rs) and to the counter electrode CNT. Preferably, the working electrode WRK is plated with platinum black and coated with glucose oxidase (GOX), the reference electrode REF is coated with silver-silver chloride, and the counter electrode is plated with platinum black. The voltage at the working electrode WRK is generally held to ground, and the voltage at the reference electrode REF is substantially held at a set voltage Vset. Vset is between 300 and 700 mV, and preferably about 535 mV.

The most prominent reaction stimulated by the voltage difference between the electrodes is the reduction of glucose as it first reacts with GOX to generate gluconic acid and hydrogen peroxide ($H_2O_2$). Then the $H_2O_2$ is reduced to water ($H_2O$) and ($O^-$) at the surface of the working electrode WRK. The $O^-$ draws a positive charge from the sensor electrical components, thus repelling an electron and causing an electrical current flow. This results in the analog current signal Isig being proportional to the concentration of glucose in the ISF that is in contact with the sensor electrodes 42. The analog current signal Isig flows from the working electrode WRK, to the counter electrode CNT, typically through a filter and back to the low rail of an op-amp 66. An input to the op-amp 66 is the set voltage Vset. The output of the op-amp 66 adjusts the counter voltage Vcnt at the counter electrode CNT as Isig changes with glucose concentration. The voltage at the working electrode WRK is generally held to ground, the voltage at the reference electrode REF is generally equal to Vset, and the voltage Vcnt at the counter electrode CNT varies as needed. In alternative embodiments, more than one sensor is used to measure blood glucose. In particular embodiments, redundant sensors are used.

In alternative embodiments, other continuous blood glucose sensors and sensor sets may be used. In particular alternative embodiments, the sensor system is a micro needle analyte sampling device such as described in U.S. patent application Ser. No. 09/460,121, filed on Dec. 13, 1999, entitled "INSERTION SET WITH MICROPIERCING MEMBERS AND METHODS OF USING THE SAME", incorporated by reference herein, or an internal glucose sensor as described in U.S. Pat. Nos. 5,497,772; 5,660,163; 5,791,344; and 5,569,186, and/or a glucose sensor that uses florescence such as described in U.S. Pat. No. 6,011,984, all of which are incorporated by reference herein.

In other alternative embodiments, the sensor system uses other sensing technologies such as described in Patent Cooperation Treaty publication No. WO 99/29230, light beams, conductivity, jet sampling, micro dialysis, microporation, ultra sonic sampling, reverse iontophoresis, or the like. In still other alternative embodiments, only the working electrode WRK is located in the subcutaneous tissue and in contact with the ISF, and the counter CNT and reference REF electrodes are located external to the body and in contact with the skin. In particular embodiments, the counter electrode CNT and the reference electrode REF are located on the surface of a monitor housing and are held to the skin as part of the telemetered characteristic monitor. In other particular embodiments, the counter electrode CNT and the reference electrode REF are held to the skin using other devices such as running a wire to the electrodes and taping the electrodes to the skin, incorporating the electrodes on the underside of a watch touching the skin, or the like. In more alternative embodiments, more than one working electrode WRK is placed into the subcutaneous tissue for redundancy. In additional alternative embodiments, a counter electrode is not used, a reference electrode REF is located outside of the body in contact with the skin (e.g., on a monitor housing), and one or more working electrodes WRK are located in the ISF. In other embodiments, ISF is harvested from the body of an individual and flowed over an external sensor that is not implanted in the body.

In preferred embodiments, the sensor cable 32 is of the type described in U.S. Patent Application Ser. No. 60/121,656, filed on Feb. 25, 1999, entitled "TEST PLUG AND CABLE FOR A GLUCOSE MONITOR", which is incorporated by reference herein. In other embodiments, other cables may be used such as shielded, low noise cables for carrying nA currents, fiber optic cables, or the like. In alternative embodiments, a short cable may be used or the sensor may be directly connected to a device without the need of a cable.

In preferred embodiments, the telemetered characteristic monitor transmitter 30 is of the type described in U.S. patent application Ser. No. 09/465,715, filed on Dec. 17, 1999, entitled "TELEMETERED CHARACTERISTIC MONITOR SYSTEM AND METHOD OF USING THE SAME" (published as PCT Application WO 00/19887 and entitled, "TELEMETERED CHARACTERISTIC MONITOR SYSTEM"), which is incorporated by reference herein, and is connected to the sensor set 28 as shown in FIGS. 3A and 3B.

In alternative embodiments, the sensor cable 32 is connected directly to the infusion device housing, as shown in FIG. 8A, which eliminates the need for a telemetered characteristic monitor transmitter 30. The infusion device contains a power supply and electrical components to operate the sensor 26 and store sensor signal values.

In other alternative embodiments, the telemetered characteristic monitor transmitter includes a receiver to receive updates or requests for additional sensor data or to receive a confirmation (a hand-shake signal) indicating that information has been received correctly. Specifically, if the telemetered characteristic monitor transmitter does not receive a confirmation signal from the infusion device, then it re-sends the information. In particular alternative embodiments, the infusion device anticipates receiving blood glucose values or other information on a periodic basis. If the expected information is not supplied when required, the infusion device sends a 'wake-up' signal to the telemetered characteristic monitor transmitter to cause it to re-send the information.

Once a sensor signal 16 is received and processed through the controller 12, commands 22 are generated to operate the infusion device 34. In preferred embodiments, semi-automated medication infusion devices of the external type are used, as generally described in U.S. Pat. Nos. 4,562,751; 4,678,408; 4,685,903; and U.S. patent application Ser. No. 09/334,858, filed on Jun. 17, 1999, entitled "EXTERNAL INFUSION DEVICE WITH REMOTE PROGRAMMING, BOLUS ESTIMATOR AND/OR VIBRATION CAPABILITIES" (published as PCT application WO 00/10628), which are herein incorporated by reference. In alternative embodiments, automated implantable medication infusion devices, as generally described in U.S. Pat. Nos. 4,373,527 and 4,573,994, are used, which are incorporated by reference herein.

In preferred embodiments, the infusion device reservoir 50 contains Humalog® lispro insulin to be infused into the body 20. Alternatively, other forms of insulin may be used such as Humalin®, human insulin, bovine insulin, porcine insulin, analogs, or other insulins such as insulin types described in U.S. Pat. No. 5,807,315, entitled "METHOD AND COMPOSITIONS FOR THE DELIVERY OF MONOMERIC PROTEINS", and U.S. Patent Application Ser. No. 60/177,897, filed on Jan. 24, 2000, entitled "MIXED BUFFER SYSTEM FOR STABILIZING POLY- PEPTIDE FORMULATIONS", which are incorporated by reference herein, or the like. In further alternative embodiments, other components are added to the insulin such as polypeptides described in U.S. patent application Ser. No. 09/334,676, filed on Jun. 25, 1999, entitled "MULTIPLE AGENT DIABETES THERAPY", small molecule insulin mimetic materials such as described in U.S. patent application Ser. No. 09/566,877, filed on May 8, 2000, entitled "DEVICE AND METHOD FOR INFUSION OF SMALL MOLECULE INSULIN MIMETIC MATERIALS", both of which are incorporated by reference herein, or the like.

In preferred embodiments, an infusion tube 36 is used to carry the insulin 24 from the infusion device 34 to the infusion set 38. In alternative embodiments, the infusion tube carries the insulin 24 from infusion device 34 directly into the body 20. In further alternative embodiments, no infusion tube is needed, for example if the infusion device is attached directly to the skin and the insulin 24 flows from the infusion device, through a cannula or needle directly into the body. In other alternative embodiments, the infusion device is internal to the body and an infusion tube may or may not be used to carry insulin away from the infusion device location.

In preferred embodiments, the infusion set 38 is of the type described in U.S. Pat. No. 4,755,173, entitled "SOFT CANNULA SUBCUTANEOUS INJECTION SET", which is incorporated by reference herein. In alternative embodiments, other infusion sets, such as the Rapid set from Desetronic, the Silhouette from MiniMed, or the like, may be used. In further alternative embodiments, no infusion set is required, for example if the infusion device is an internal infusion device or if the infusion device is attached directly to the skin.

In further alternative embodiments, the pre-filter, filters, calibrator and/or controller 12 are located in a supplemental device that is in communication with both the telemetered characteristic monitor transmitter 30 and the infusion device 34. Examples of supplemental devices include a hand held personal digital assistant such as described in U.S. patent application Ser. No. 09/487,423, filed on Jan. 20, 2000, entitled "HANDHELD PERSONAL DATA ASSISTANT (PDA) WITH A MEDICAL DEVICE AND METHOD OF USING THE SAME", which is incorporated by reference herein, a computer, a module that may be attached to the telemetered characteristic monitor transmitter 30, a module that may be attached to the infusion device 34, a RF programmer such as described in U.S. patent application Ser. No. 09/334,858, filed on Jun. 17, 1999, entitled "EXTERNAL INFUSION DEVICE WITH REMOTE PROGRAMMING, BOLUS ESTIMATOR AND/OR VIBRATION CAPABILITIES" (published as PCT application WO 00/10628), which is incorporated by reference herein, or the like. In particular embodiments, the supplemental device includes a post-calibration filter, a display, a recorder, and/or a blood glucose meter. In further alternative embodiments, the supplemental device includes a method and means for a user to add or modify information to be communicated to the infusion device 34 and/or the telemetered characteristic monitor transmitter 30 such as buttons, a keyboard, a touch screen, a voice-recognition device, and the like.

In preferred embodiments, the controller 12 is designed to model a pancreatic beta cell (β-cell). In other words, the controller 12 commands the infusion device 34 to release insulin 24 into the body 20 at a rate that causes the insulin concentration in the blood to follow a similar concentration profile as would be caused by fully functioning human β-cells responding to blood glucose concentrations in the body 20.

A controller that simulates the body's natural insulin response to blood glucose levels not only makes efficient use of insulin but also accounts for other bodily functions as well since insulin has both metabolic and mitogenic effects. Controller algorithms that are designed to minimize glucose excursions in the body without regard for how much insulin is delivered may cause excessive weight gain, hypertension, and atherosclerosis. Similarly, algorithms that are designed to minimize glucose excursions in the body without regard for the time period over which the glucose excursion may occur, or the time period over which the insulin is delivered and/or the insulin-delivery pattern, may lead to hypoglycemia, thereby causing dizziness, or, in severe cases, death. Therefore, in preferred embodiments of the present invention, the controller 12 is intended to emulate the in vivo insulin secretion pattern and to adjust this pattern to be consistent with in vivo β-cell adaptation. The in vivo β-cell response in subjects with normal glucose tolerance (NGT), with widely varying insulin sensitivity ($S_I$), is the optimal insulin response for the maintenance of glucose homeostasis.

Generally, in a normally glucose tolerant human body, healthy β-cells benefit from such inputs as neural stimulation, gut hormone stimulation, changes in free fatty acid (FFA) and protein stimulation, etc. Thus, in preferred embodiments, the user may manually input into the controller 12 supplemental information such as a start of a meal, an anticipated carbohydrate content of the meal, a start of a sleep cycle, anticipated sleep duration, anticipated exercise duration and intensity, or the like. Then, a model predictive estimator (MPE) feature assists the controller to use the supplemental information to anticipate changes in glucose concentration and modify the insulin delivery accordingly. For example, in a NGT individual, neural stimulation triggers the β-cells to begin to secrete insulin into the blood stream before a meal begins, which is well before the blood glucose concentration begins to rise. So, in alternative embodiments, the user can tell the system that a meal is beginning and the pump will deliver insulin in anticipation of the meal. In a more preferred embodiment, the controller is a Model Predictive Controller (MPC) that uses a model of subsequent outcomes to control and supervise the operation of a diabetes-management system in such a way as to optimize delivery of insulin to a user's body to compensate for β-cells that perform inadequately.

Thus, embodiments of the present invention are directed to a mathematical metabolic model that is used in conjunction with a model predictive estimator to replicate insulin and glucose kinetics and dynamics so as to mimic true physiological profiles. These profiles may then be used to optimize decisions about bolus amounts, insulin-delivery patterns, timing of insulin delivery, and the overall operational efficiency of the diabetes-management system. Thus, in a closed-loop system, for example, the controller 12 may perform this optimization and provide appropriate delivery commands 22 to the infusion device. In a semi-closed loop system, on the other hand, the profiles created by the controller may be displayed on the infusion device, such that the user/patient can adopt the best strategy (i.e., glucose profile) and then instruct the controller or infusion device accordingly.

The mathematical metabolic model according to the preferred embodiment of the invention comprises three sets of equations which relate, respectively, to: (1) a "Minimal Model" that describes the change in glucose concentration (G), and the proportional reduction of glucose disappearance due to insulin (Y), as a function of time; (2) a "Pump Delivery to Plasma Insulin Model", which is a two-compartment model that derives plasma insulin concentrations from pump delivery (thereby describing the change over time of insulin concentration in the plasma ($I_P$) and of insulin concentration in the remote compartment ($I_R$)); and (3) a "Meal Appearance Rate Model", which is also a two-compartment model (with the same time constant) that describes the rate of appearance of a meal ($R_A$).

Specifically, each of the Minimal Model, the Pump Delivery to Plasma Insulin Model, and the Meal Appearance Rate Model may be described mathematically as follows:

Minimal Model $$\frac{dG}{dt}(t) = -(GEZI + S_I * Y) * G(t) + p_4 + R_A(t) \quad \text{Eqn. (1)}$$

$$\frac{dY}{dt}(t) = p_2 * (-Y(t) + I_P(t)) \quad \text{Eqn. (2)}$$

Pump Delivery to Plasma Insulin Model $$\frac{dI_R}{dt}(t) = \frac{1}{\tau_1} * \left(-I_R(t) + \frac{\frac{R_B(t)}{60}}{C_I * 10^{-6}}\right) \quad \text{Eqn. (3)}$$

$$\frac{dI_P}{dt}(t) = \frac{1}{\tau_2} * (-I_P(t) + I_R(t)) \text{ (normalized)} \quad \text{Eqn. (4)}$$

Meal Appearance Rate Model $$R_A(t) = \frac{C_H}{V_G * \tau_m^2} * e^{-\frac{t}{\tau_m}} \quad \text{Eqn. (5)}$$

Wherein the following variables are defined as:
Y: Proportional reduction of glucose disappearance due to insulin (unitless)
$R_A$: Exogenous meal appearance rate (mg/dl/min)
$I_P$: Insulin concentration in the plasma (μU/ml)
$I_R$: Insulin concentration in the remote compartment (μU/ml)
$C_I$: Insulin clearance (ml/min)
And the following parameters are defined as:
GEZI: Glucose effectiveness at zero insulin
$p_2$: Insulin action time constant
$S_I$: Insulin Sensitivity
$p_4$: Endogenous glucose production
$\tau_1$: Insulin time constant out of the remote compartment
$\tau_2$: Insulin time constant out of the plasma space
$V_G$: Glucose distribution volume
$\tau_m$: Time constants for meal out of the first and second compartments (this is equivalent to the peak time of the meal appearance rate curve)
$C_H$: Carbohydrate ingested
$I_{SB}$: Insulin given as a single bolus for a meal
$T_D$: Time duration of extended bolus Embodiments of the present invention are directed to model predictive techniques that may utilize the above mathematical metabolic model in at least three ways: (1) as a model predictive bolus estimator (MPBE) in a method of optimizing delivery of insulin into a body of a user to cover a planned meal (see FIG. 10); (2) as a model predictive supervisor (MPS) in a method of monitoring the operation of a diabetes-management system (see FIG. 14); and (3) as a model predictive controller (MPC) in a method of optimizing the delivery of insulin into the body of a user so as to achieve a desired blood glucose concentration (see FIG. 16). These embodiments—which, in the ensuing discussion, are referred to as the "first", "second", and "third" embodiment, respectively—will be described below in conjunction with a specific example. It will be understood, however, that the specific example is provided by way of illustration only, and not limitation.

For the specific illustrative example, the following fit parameters were used:

| | |
|---|---|
| GEZI: $3.69*10^{-4}$ $\text{min}^{-1}$ | Glucose effectiveness at zero insulin |
| $P_2$: 0.01 $\text{min}^{-1}$ | Insulin action time constant |
| $S_I$: $3.23*10^{-4}$ ml/μU/min | Insulin Sensitivity |
| $P_4$: 0.606 mg/dl/min | Endogenous glucose production |
| $\tau_1$: 45.26 min | Insulin time constant out of the remote compartment |
| $\tau_2$: 45.35 min | Insulin time constant out of the plasma space |
| $V_G$: 209.46 dl | Glucose distribution volume |
| $\tau_m$: 15, 60, & 200 min | Time constants for meal out of the first and second compartments, where each specific value is equivalent to the peak time of the meal appearance rate curve |
| $C_H$: 50000 mg | Carbohydrate ingested |
| $I_{SB}$: 3U | Insulin given as a single bolus for a meal |
| $T_D$: 2 or 4 hrs | Time duration of extended bolus |

Solving Equations (1)-(5) for the initial conditions, i.e., steady-state conditions immediately prior to the time of administering a meal bolus at time t=0, yields:

$$G(0) = \frac{p_4}{(GEZI + p_2 * Y(0))} \quad \text{Eqn. (6)}$$

$$Y(0) = S_I * I_P(0) \quad \text{Eqn. (7)}$$

$$I_R(0) = \frac{1}{C_I * 10^{-6}} * \left(\frac{R_B(0)}{60} + \frac{1}{\tau_1} * B_I(0)\right) \quad \text{Eqn. (8)}$$

$$I_P(0) = \frac{\frac{R_B(0)}{60}}{C_I * 10^{-6}} \quad \text{Eqn. (9)}$$

Figure 10:
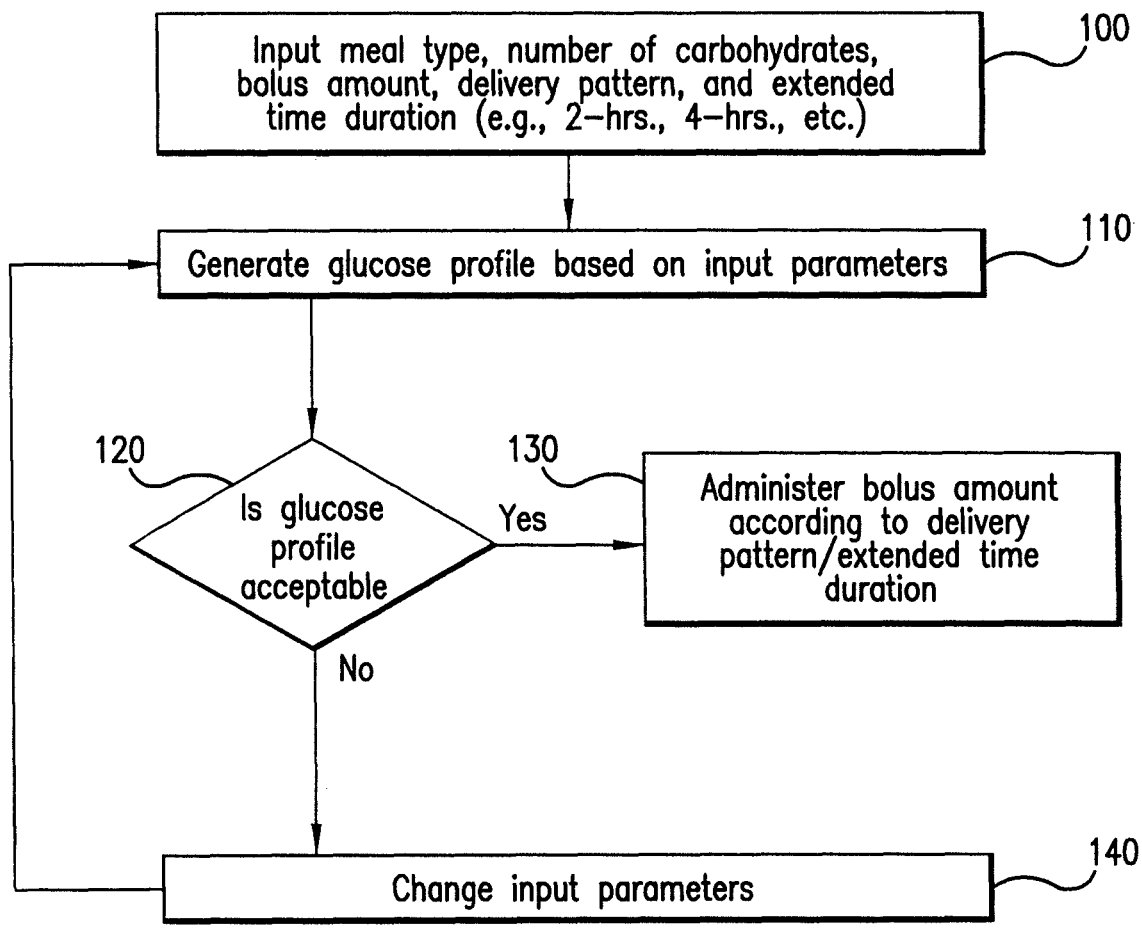
FIG. 10 illustrates an algorithm for optimizing delivery of insulin into a body of a user to cover a planned meal in accordance with an embodiment of the present invention.

The first embodiment, involving a model predictive bolus estimator will now be described with reference to FIG. 10. In this embodiment, the basic inquiry may be summarized as follows: For the same amount of insulin delivered to compensate for a meal (i.e., where the areas under the respective plasma insulin curves are the same), how do the postprandial glucose (PPG) profiles compare for different distributions, or delivery patterns, of insulin?

With the above in mind, the process of optimizing the delivery of insulin into the body of a patient to cover a planned meal thus starts with identifying values for the input parameters at block 100. This includes the fit parameters noted above. Thus, for example, the anticipated meal is assumed to have 50 g of carbohydrates, and the bolus amount ($I_{SB}$) is taken to be 3 U. In addition, three meal types have been identified, wherein a "fast meal" has a time constant $\tau_m$ of 15 minutes, a "medium meal" has a time constant $\tau_m$ of 60 minutes, and a "slow meal" has a time constant $\tau_m$ of 200 minutes.

In addition, $R_B(0)$ is set to 1.6 U/hr in accordance with the fit parameters in order to start the glucose concentration at 100 mg/dl. The assumption, for the purposes of this example, is that the patient has the correct basal rate prior to the meal, thereby yielding a starting glucose at euglycemia. Moreover, the amount of insulin given to cover the meal with a carbohydrate content of 50 g was determined by the total number of units necessary for a single bolus to yield a peak PPG concentration of 180 mg/dl (i.e., the maximum peak PPG per ADA guidelines) for the typical "medium meal" $R_A$ (peak at 60 min).

It is noted that, in answering the basic inquiry noted above, various insulin delivery patterns may be modeled using the model predictive estimator. For example, a user may wish to compare the (postprandial, post-infusion) glucose profiles that would result if the 3 U of insulin were delivered as a single bolus at the time of the meal, as opposed to an "extended bolus", where a portion of the bolus is delivered at the time of the meal, and the remainder is delivered uniformly over a period of time. For the purposes of the specific example used herein, three delivery patterns, and two extended periods of time, were used. The delivery patterns include: (1) a basal delivery, wherein no additional bolus is administered in view of the user's consumption of the meal; (2) a single-bolus delivery, wherein the entirety of the 3 U of insulin is delivered at time t=0, i.e., at the time of the meal; and (3) an extended bolus delivery, wherein it was assumed that 50% of the bolus was delivered at time t=0, and the remaining 50% was delivered uniformly over an extended period of time (and in addition to the meal-independent basal rate of 1.6 U/hr). It should be understood, however, that for extended bolus delivery, the bolus may be delivered in various proportions other than 50%-50%. Also, for the illustrative example, the time duration of the extended bolus ($T_D$) was allowed to be either 2 hours or 4 hours. Again, any other time period may also be used.

Figure 11:
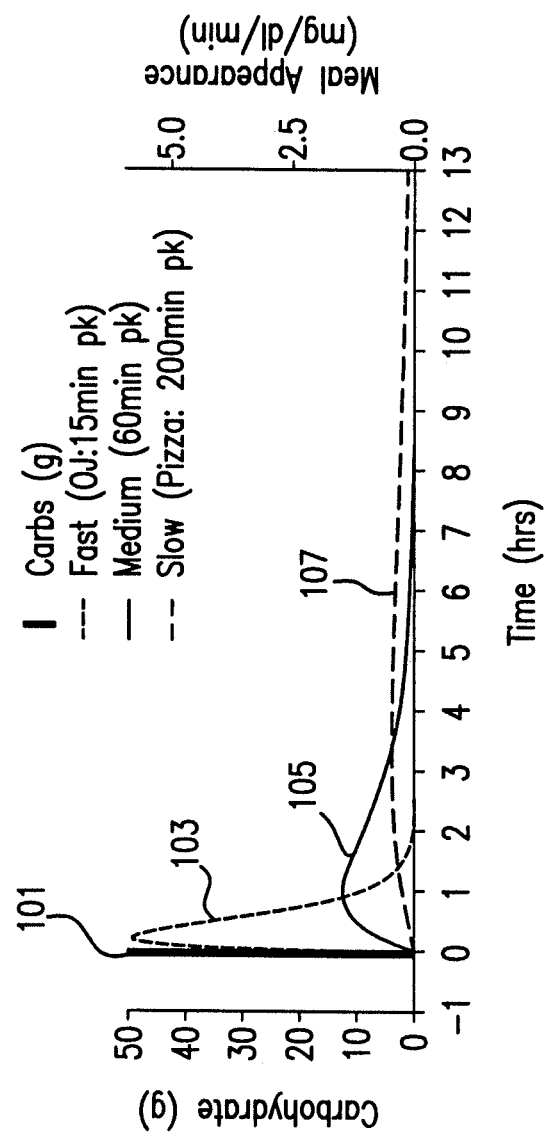
FIG. 11 shows meal appearance curves for three different meal types in accordance with an embodiment of the present invention.

Referring back to FIG. 10, using the above input parameters with Eqns. (1)-(5), glucose profiles can now be generated at block 110. More specifically, Eqn. (5) may first be used to generate meal appearance profiles for the various meal types. As noted before, the meals simulated for this example were: a meal with a fast rate of appearance (e.g., orange juice: 15 min. $R_A$ peak); a meal with a medium rate of appearance (e.g., salad: 60 min. $R_A$ peak); and a meal with a slow rate of appearance (e.g., pizza: 200 min. $R_A$ peak). Thus, as shown in FIG. 11, the 50 g carbohydrate content 101 for each meal is assumed to have been consumed at time t=0, with the curve 103 for the fast meal peaking at about time t=15 min., the curve 105 for the medium meal peaking at about time t=1 hr., and the curve 107 for the slow meal peaking at about t=3.3 hrs. As can be seen from the Minimal Model, the exogenous meal appearance rate $R_A$ of Eqn. (5) will subsequently be used as an input in Eqn. (1).

Figure 12A:
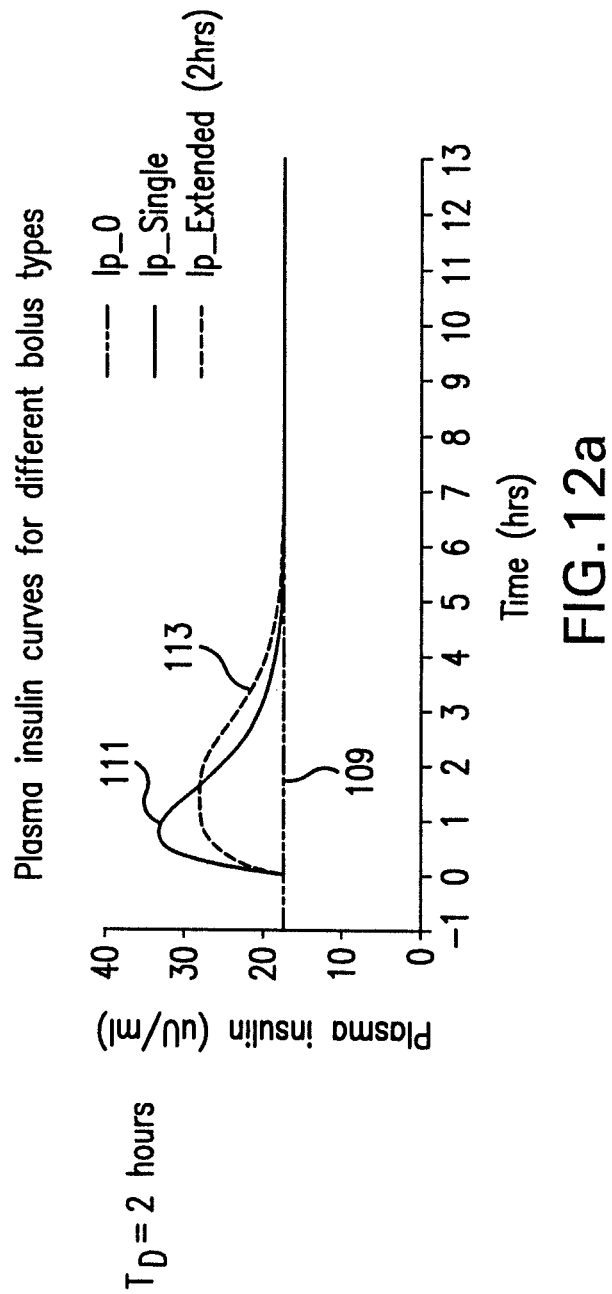
FIG. 12A shows plasma insulin concentration curves for three different delivery patterns in accordance with an embodiment of the present invention.
Figure 13A:
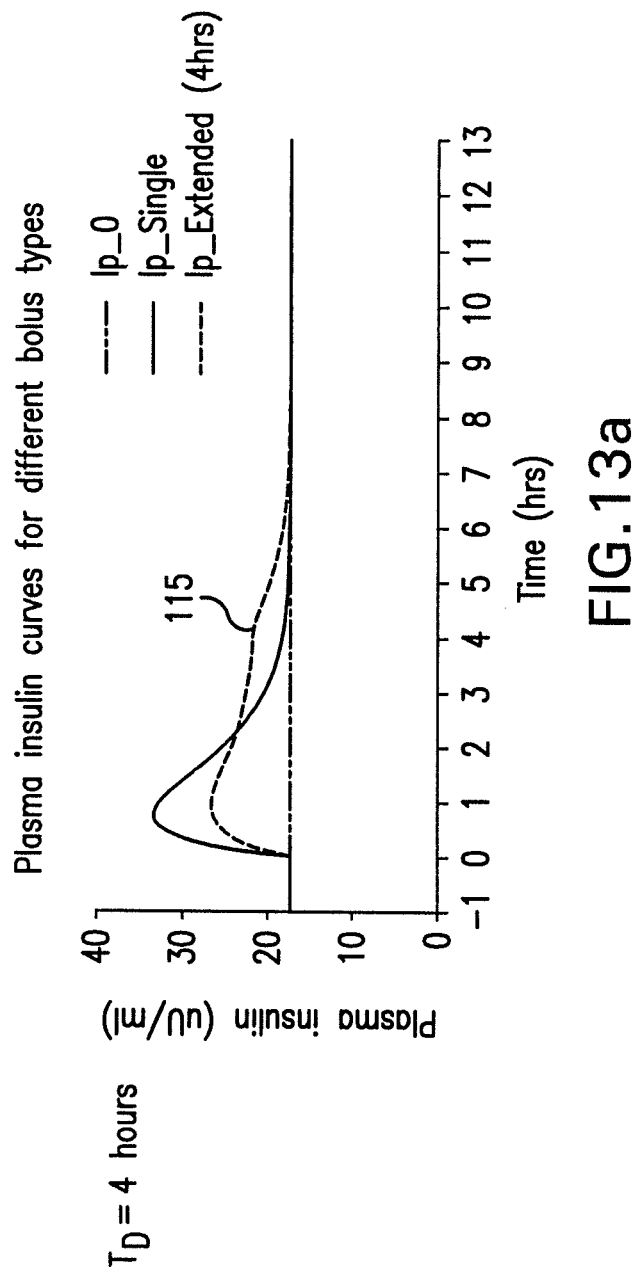
FIG. 13A shows a second set of plasma insulin concentration curves for three different delivery patterns in accordance with an embodiment of the present invention.

Next, Eqns. (3) and (4)—that is, the Pump Delivery to Plasma Insulin Model—may be used to generate plasma insulin profiles for the various delivery patterns. For the example herein, FIG. 12A shows the plasma insulin curves for the basal pattern 109, the single-bolus pattern 111, and the 2-hour extended bolus pattern 113. FIG. 13A shows the plasma insulin curve for the 4-hour extended bolus pattern 115. As noted previously, because they provide the user with an indication of whether plasma insulin concentration is decreasing or increasing, FIGS. 12A and 13A are more informative for the user than an indication of insulin on board alone. As such, the Pump Delivery to Plasma Insulin Model provides the user with a more powerful tool in deciding if, or when, additional insulin should be administered.

Figure 12D:
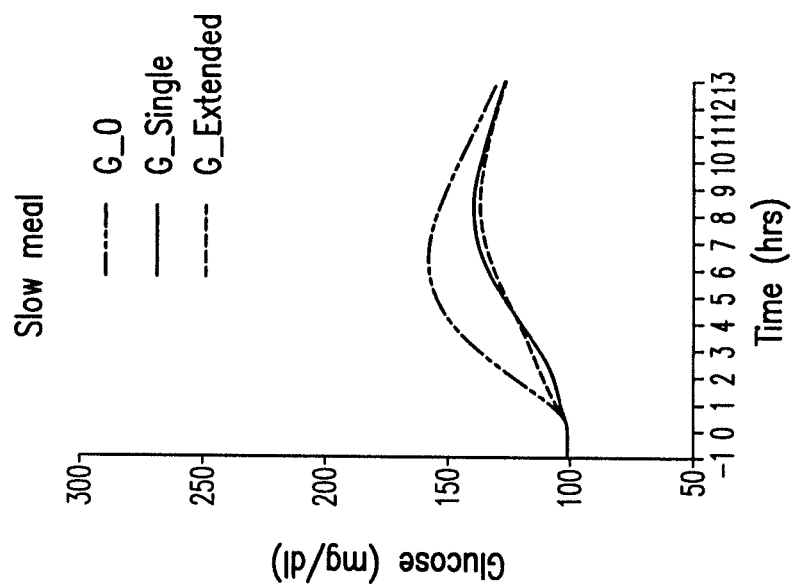
FIG. 12D shows glucose concentration profiles for a slow meal in accordance with an embodiment of the present invention.
Figure 12C:
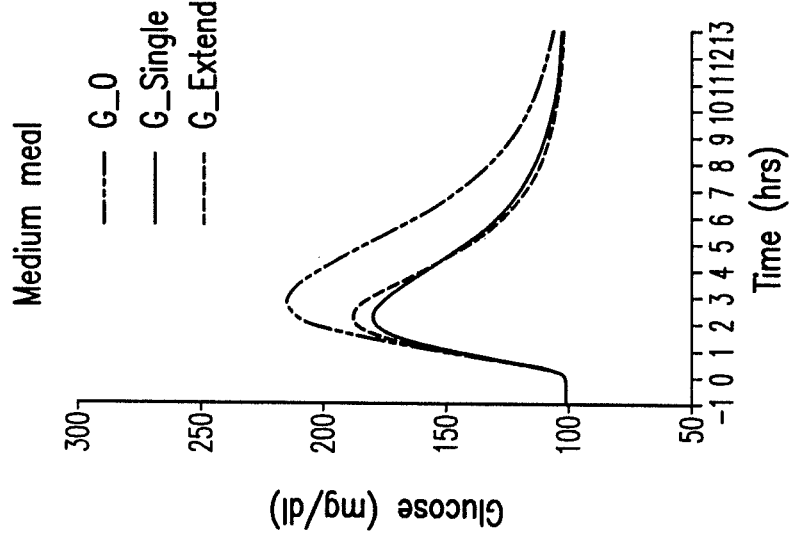
FIG. 12C shows glucose concentration profiles for a medium meal in accordance with an embodiment of the present invention.
Figure 12B:
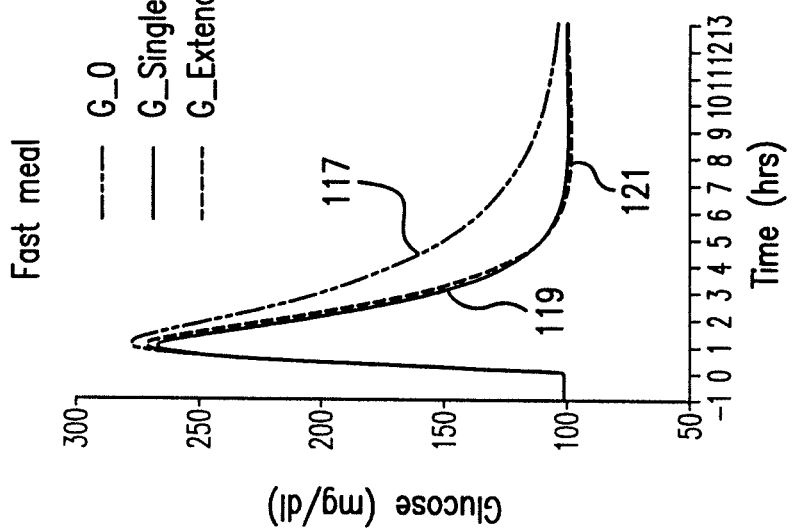
FIG. 12B shows glucose concentration profiles for a fast meal in accordance with an embodiment of the present invention.
Figure 13D:
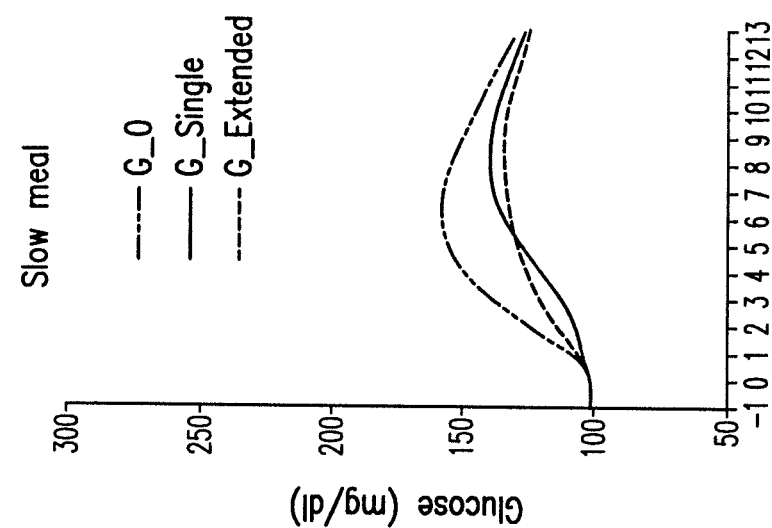
FIG. 13D shows a second set of glucose concentration profiles for a slow meal in accordance with an embodiment of the present invention.
Figure 13C:
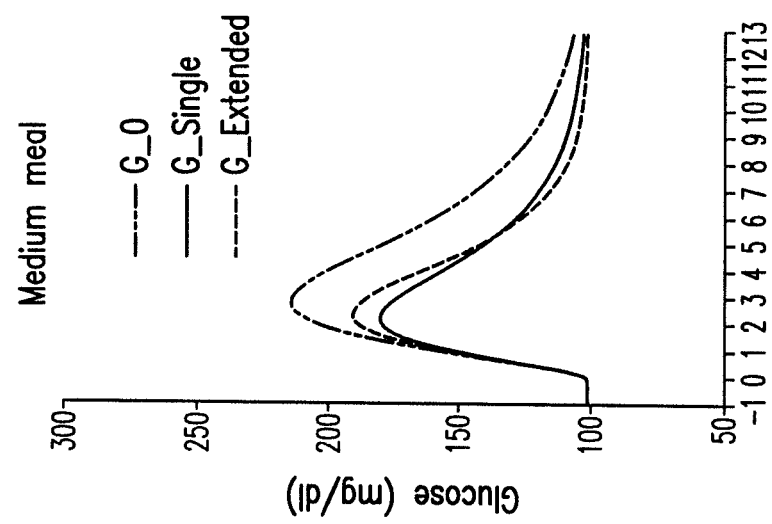
FIG. 13C shows a second set of glucose concentration profiles for a medium meal in accordance with an embodiment of the present invention.
Figure 13B:
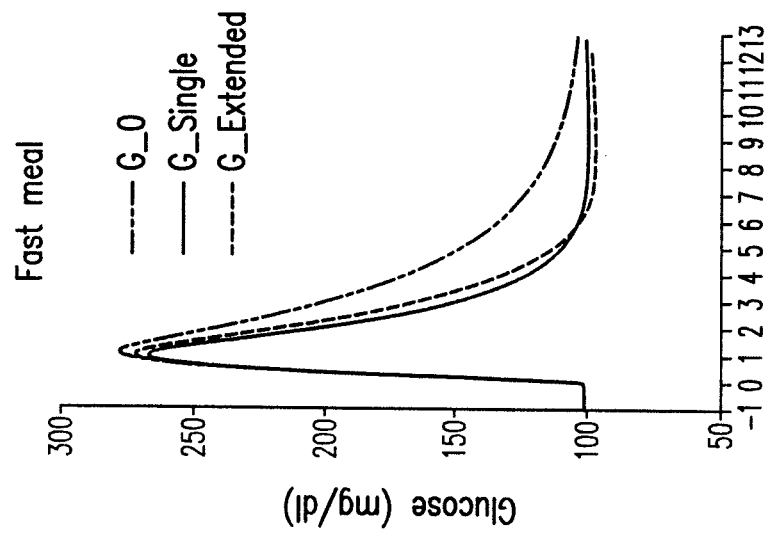
FIG. 13B shows a second set of glucose concentration profiles for a fast meal in accordance with an embodiment of the present invention.

Next, Eqns. (1) and (2) are used to generate the glucose profiles. Thus, for example, FIG. 12B shows the glucose profile for each of a basal delivery 117, a single-bolus delivery 119, and a 2-hour extended delivery 121 for a fast meal. FIGS. 12C and 12D show the glucose profiles for the same three delivery patterns, assuming, respectively, a medium absorbing meal, and a slow absorbing meal. Similarly, FIGS. 13B-13D show the glucose profiles assuming all three delivery profiles for each meal type, except that the time duration of the extended bolus is now 4 hours.

Once the glucose profiles for all combinations of delivery pattern and meal type have been generated, the algorithm then inquires, at block 120, whether a specific glucose profile is acceptable. Thus, in a semi-closed loop system, for example, the above-noted glucose profiles may be displayed on the controller, the pump, etc., and the user may be asked to provide approval of one of the glucose profiles. In the illustrative example, the user might have inquired as to all three meal types in order to decide which meal to consume. Having seen the resultant postprandial glucose profiles, the user can now decide whether any one of them would be acceptable.

If the user finds that none of the generated glucose profiles is acceptable, he may opt to change one or more of the input parameters (block 140), and run the algorithm again. Thus, the user may decide, for example, that a different bolus amount ($I_{SB}$) should be used. Or, the user may wish to input a different "type" of meal, i.e., one having a peak rate that is different from the three that were previously modeled. Similarly, for the extended delivery pattern, the user may wish to consider different proportions for the immediate vs. extended-delivery phases of insulin administration. The algorithm can therefore be implemented iteratively, until an acceptable glucose profile has been found. It is noted that, in a closed-loop system, the same logic may be used, where acceptability may be determined by, e.g., comparing the generated glucose profiles to a pre-defined profile, such as one that is derived in accordance with ADA guidelines for the given input parameters.

Once one of the glucose profiles has been approved, insulin is delivered, at block 130, to the user according to the delivery pattern and extended-time duration, if any, of the accepted profile. Thus, upon the user's indication of approval, and/or upon the controller's determination that one of the glucose profiles is within acceptable range of a pre-defined profile, the controller 12 generates and transmits commands 22 to the insulin delivery system 14 to deliver insulin to the user's body accordingly. See FIG. 1.

Figure 14:
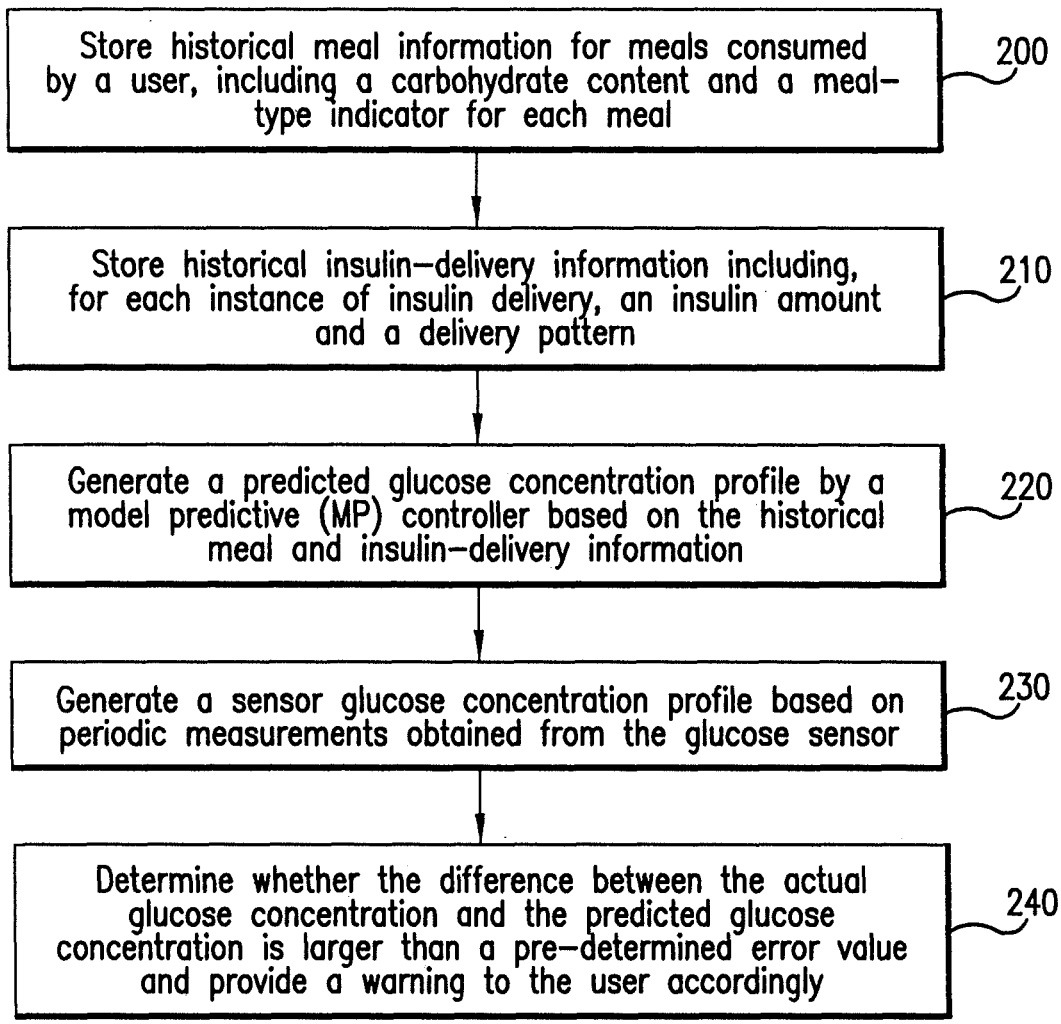
FIG. 14 illustrates an algorithm for monitoring the operation of a diabetes-management system in accordance with an embodiment of the present invention.

The second embodiment noted above, which is directed to a method of monitoring the operation of the diabetes-management system using a model predictive supervisor, will now be described with reference to FIGS. 14 and 15.

Figure 15A:
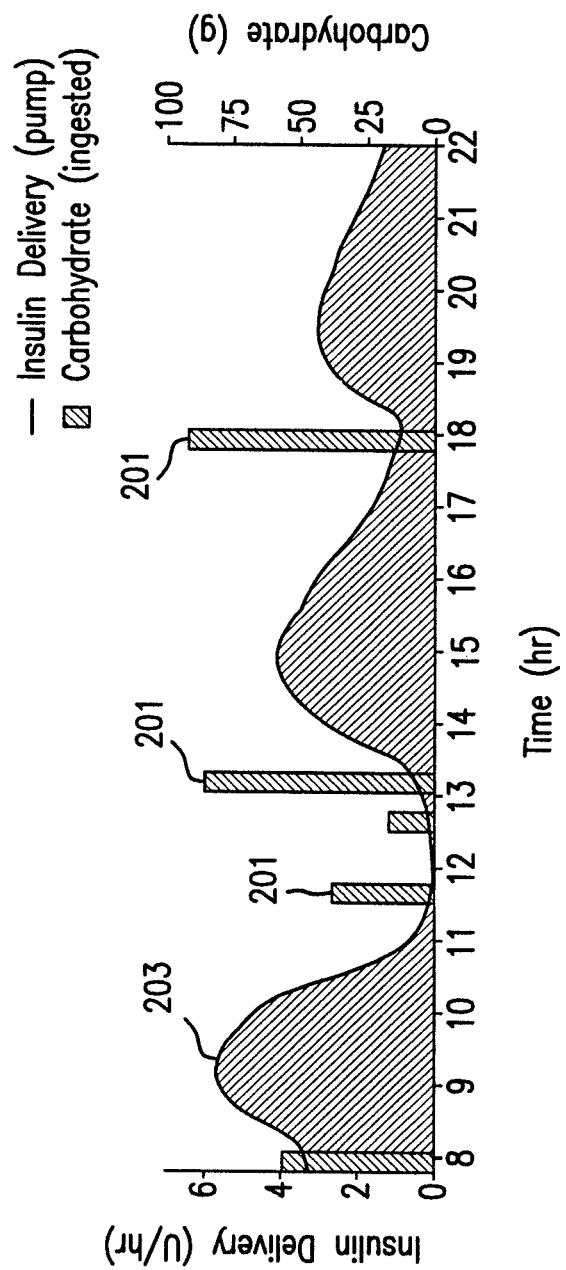
FIG. 15A shows historical insulin delivery and consumed meal data according to an embodiment of the present invention.

The algorithm starts at block 200, wherein historical meal information, including the carbohydrate content and a meal-type indicator for each meal consumed by a user is stored. As with the first embodiment, the meal-type indicator may be the "type" of meal, e.g., a fast meal. In this case, the estimator will then associate the meal-type with an average peak time for the appearance rate of that "type" of meal, e.g., 200 minutes for a fast meal. Alternatively, the meal-type indicator may be the estimated peak time for the meal's appearance rate. Similarly, block 210 calls for storage of historical insulin-delivery information including, for each instance of insulin delivery, an insulin amount and a delivery pattern. FIG. 15A is a graphical depiction of historical carbohydrate 201 and insulin delivery 203 information for a simulated example.

Figure 15B:
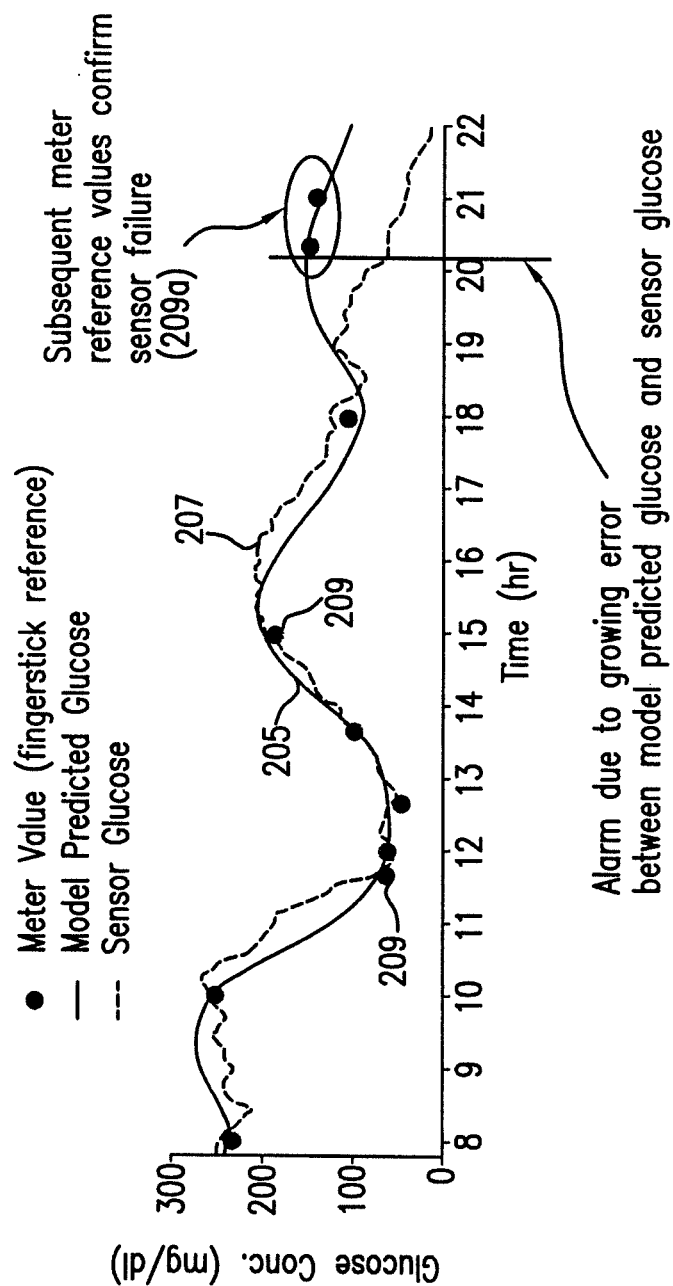
FIG. 15B shows predicted and sensor glucose profiles in accordance with an embodiment of the present invention.

With the above information, and utilizing the Metabolic Model as with the first embodiment, the model predictive estimator then generates, at block 220, a predicted glucose concentration profile. In FIG. 15B, this is shown with reference numeral 205. As described previously, in embodiments of the invention, the sensor 26 is used to obtain periodic (e.g., once every five minutes) measurements of the user's glucose concentration. Thus, along with the predicted glucose profile, a sensor glucose concentration profile is generated (block 230) based on the above-mentioned periodic measurements.

Then, as called for in block 240, the predicted glucose profile 205 and the sensor glucose profile 207 are compared, either periodically or on a continuous basis, to determine whether, for a given point in time, the difference between the sensor glucose concentration value and the predicted glucose concentration value is larger than a pre-determined error value. If the latter condition is met, then the controller and/or the pump provides a warning to the user which may include, e.g., an audible alarm, a visual signal, a vibrating indicator, or any combinations thereof.

As noted above, the controller may be configured to generate a warning for any single occurrence of an excessive amount of disparity between the predicted and sensor glucose concentrations. In a variation of this embodiment, however, historical data may be stored for the magnitude of the above-mentioned disparity. Then, the controller may generate a warning when each of a pre-selected number of successive comparisons yields a disparity between the predicted and sensor profiles that is greater than the pre-determined error value. In yet another alternative aspect, a warning may be generated when the controller detects a trend of increasing disparities for a plurality of successive comparisons.

The glucose profiles 205, 207 may be displayed for the user, e.g., on the pump. As shown in FIG. 15B, glucose meter measurements 209 obtained from fingerstick tests may also be displayed. Thus, for the simulation shown in FIG. 15B, a warning may be generated at some point after 19 hours, depending on the magnitude of the predetermined error value and/or the configuration of the controller (as discussed above in connection with alternative aspects of this embodiment). For example, a warning may be provided to the user shortly after 20 hours, at which point the disparity, or discrepancy, between the predicted glucose profile 205 and the sensor glucose profile 207 has been growing for about an hour.

In practice, the warning would prompt the user to check for faulty components, such as, e.g., a sensor, an insulin catheter, or a pump component. For example, as shown in FIG. 15B, upon, or shortly after, receiving the warning, the user may conduct one or more fingerstick tests, with meter readings 209a which may also be displayed. Meter readings that coincide with, or are very close to, the predicted profile 205—and thus vastly different from the sensor profile 207—would then confirm that the sensor has failed and must be replaced. If, on the other hand, the meter readings 209a agree with the sensor profile 207, this may be an indication that the user might have entered the carbohydrate content of a recent meal incorrectly, or that a model inaccuracy may be producing an erroneous predicted glucose profile. In these, and other similar situations, the warning provided to the user would allow monitoring of the operation of the system, and correction of system or user failures, on a real-time basis.

Figure 16:
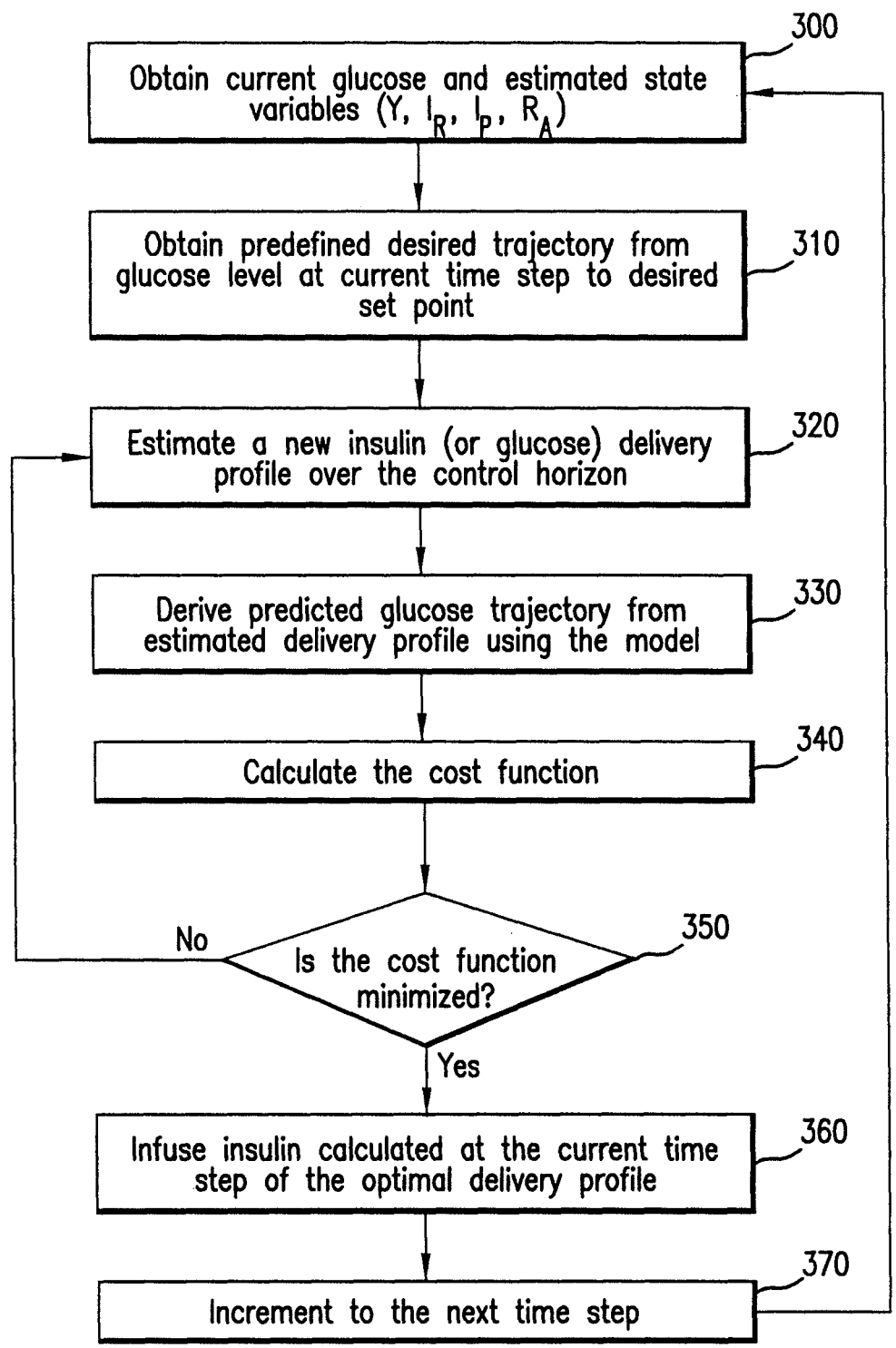
FIG. 16 illustrates an algorithm for optimizing the delivery of insulin into the body of a user for achieving a desired blood glucose concentration according to an embodiment of the present invention.

The third embodiment is directed to a model predictive controller (MPC) for optimizing the delivery of insulin into the user's body, so as to achieve a desired blood glucose concentration, by considering not only historical insulin-delivery data and the current state of the user's body, but also the future effect of insulin delivered to the user's body. As shown in FIG. 16, the algorithm starts at block 300 by measuring the user's current blood glucose concentration. At block 310, a pre-defined desired glucose trajectory is generated as the optimal profile that starts at the current glucose state and approaches a desired steady state setpoint. In embodiments of the invention, the pre-defined glucose profile, or trajectory, may be determined pursuant to ADA guidelines for achieving a desired (goal) value of glucose concentration given the current glucose concentration value. In alternative embodiments, the desired glucose trajectory may be defined in any manner that would minimize rapid fluctuations, shock to the body, etc.

Figure 17:
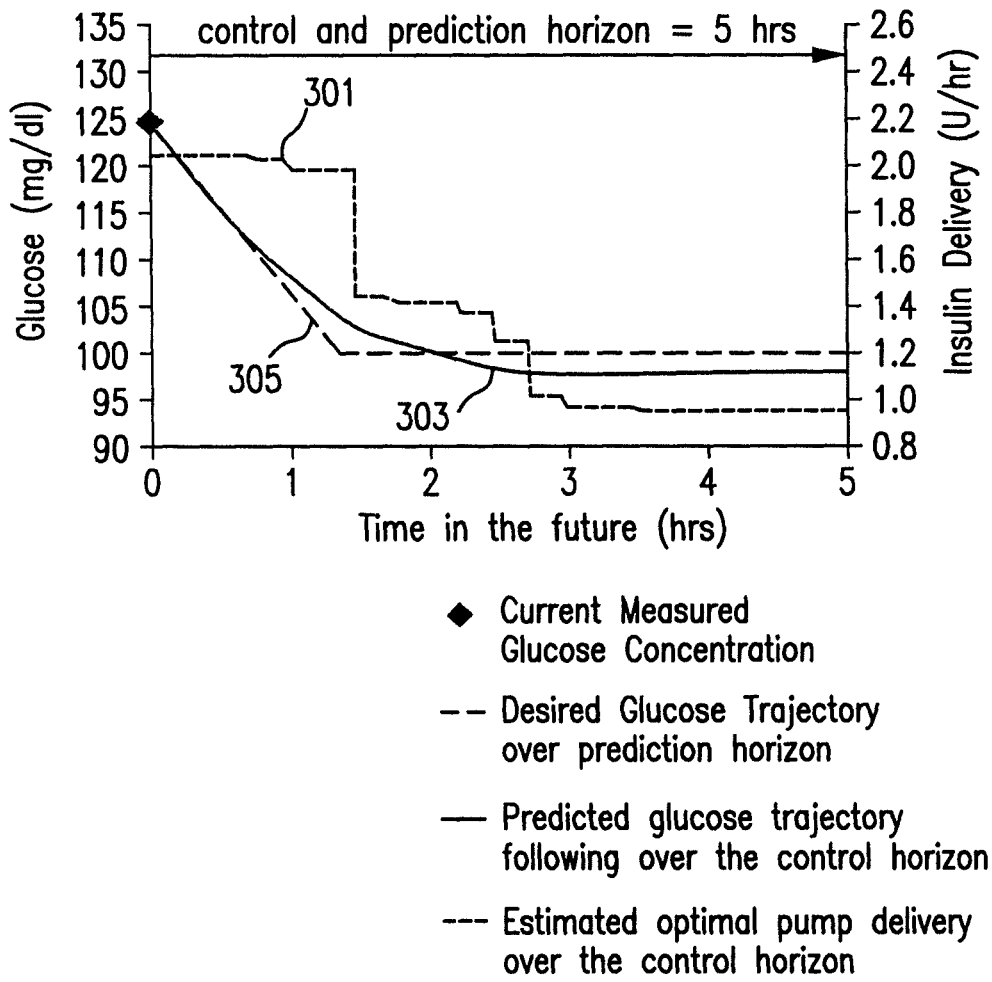
FIG. 17 shows estimated insulin delivery, predicted glucose concentration, and desired glucose concentration profiles in accordance with an embodiment of the present invention.

The algorithm then proceeds to block 320, where an estimated insulin-delivery profile is generated that would attempt to achieve the desired glucose concentration value over a predetermined time period, which may be referred to as the control horizon. Next, at block 330, the metabolic model of the MPC algorithm is used to generate a predicted glucose concentration profile over a prediction horizon based on the current glucose concentration and the generated insulin-delivery profile. FIG. 17 shows a simulation in which the control horizon and prediction horizon are both 5 hours long, the current glucose level (i.e., 125 mg/dl) is higher than the desired glucose level (i.e., 100 mg/dl), the estimated insulin delivery profile is designated by reference numeral 301, the predicted glucose concentration profile is designated by reference numeral 303, and the desired glucose trajectory is shown using reference numeral 305.

Once the predicted glucose profile 303 has been generated, it is compared to the pre-defined glucose profile. At this point in the process, the goal is to minimize the difference between the predicted glucose profile 303 and the pre-defined desired glucose profile 305 in such a way as to ensure that the future estimated insulin delivery profile 301 is optimized. Put another way, the algorithm aims to optimize the estimated insulin delivery profile 301 so as to generate a predicted glucose concentration profile 303 that is as close as possible to the desired glucose concentration profile 305. To achieve this goal, embodiments of the invention may utilize an optimization process wherein an error function that describes the error, or difference, between the predicted glucose profile 303 and the desired glucose profile 305 is minimized.

In embodiments of the invention, the optimization process may employ a penalty function in addition to the error function noted above; the mathematical sum of the error function and the penalty function may be referred to as a cost function. In practice, whereas the error function simply addresses the difference between the predicted and desired glucose profiles, the penalty function provides a check against sudden changes in insulin delivery and/or large increases in the total amount of insulin delivered. Therefore, where a cost function is employed, optimization of the estimated insulin delivery profile 301 entails minimization of the entire cost function to not only ensure minimal error, but also avoid sudden changes in insulin delivery/amount.

With reference to the metabolic model discussed previously, Equation 10 shows one representative cost function that may be used by the model predictive control algorithm:

$$\sum_{i=0}^{N_P-1} \left(\hat{G}(k+i) - G_D(k)\right)^2 + 1/\rho \sum_{i=0}^{N_C-1} \left(\hat{I}_D(k+i) - \hat{I}_D(k+i-1)\right)^2 \quad \text{Eqn. (10)}$$

Wherein:
$N_P$: Number of samples in prediction horizon
$N_C$: Number of samples in control horizon
$\hat{G}$: Estimated future glucose concentration
$G_D$: Desired future glucose concentration
$\hat{I}_D$: Estimated future insulin delivery rate
$\rho$: Weight that determines relative importance of achieving the desired glucose profile versus the penalty in changing the insulin delivery rate In the above equation, the first half of the expression is an error function expressed in terms of the sum squared difference between the predicted glucose concentration profile and the pre-defined glucose concentration profile. The second half of the expression, on the other hand, represents a penalty function that discourages sudden changes in insulin delivery and provides a penalty for utilizing too much insulin to achieve the desired glucose profile. It is noted that, in alternative embodiments, the error function may be defined differently than that shown in Eqn. (10), while still accounting for the difference between the predicted and desired glucose profiles. Similarly, when used, the penalty function may be defined differently and/or may include fewer or more terms than those reflected in Eqn. (10), depending on the number of process variables that need to be controlled.

Returning to FIG. 16, and assuming the optimization process utilizes a cost function, in block 340, the algorithm calculates the cost function (e.g., Eqn. (10)), and then determines whether the cost function is minimized for the proposed insulin delivery profile (block 350). If the cost function is minimized, then a command is generated for the pump to deliver insulin at a rate calculated at the current time step based on the delivery profile which resulted in the acceptable glucose concentration profile (block 360). If, on the other hand, the cost function is not minimized, then the algorithm loops back to block 320, where it generates a new insulin delivery profile, based on which a new glucose profile is generated. This process is repeated iteratively until the cost function is minimized at block 350. By minimizing the entire cost function, the MPC weighs the behavior of the insulin delivery profile in its goal to minimize the sum squared difference between the a priori predicted glucose trajectory and the desired profile.

As noted previously, once the minimal cost function has been found, a command is generated at block 360 for the pump to deliver insulin at a rate calculated at the current time step based on the (optimal) insulin delivery profile which resulted in the acceptable (predicted) glucose concentration profile. The insulin is then delivered for a pre-set period of time, or time step. In embodiments of the invention, each time step is on the order of minutes, such as, e.g., 5 minutes. At the next time step, the algorithm loops back to block 300, and the process is repeated.

While the description above refers to particular embodiments of the present invention, it will be understood that many modifications may be made without departing from the spirit thereof. The accompanying claims are intended to cover such modifications as would fall within the true scope and spirit of the present invention.

The presently disclosed embodiments are therefore to be considered in all respects as illustrative and not restrictive, the scope of the invention being indicated by the appended claims, rather than the foregoing description, and all changes which come within the meaning and range of equivalency of the claims are therefore intended to be embraced therein.

What is claimed is:

1. A processor-implemented method comprising:
   obtaining a current glucose value for a user of an insulin delivery device;
   generating a desired glucose trajectory that approaches a desired steady state setpoint from the current glucose value over a prediction horizon;
   generating an insulin delivery pattern corresponding to an amount of insulin to be delivered to the user over a control horizon;
   generating a predicted glucose trajectory over the control horizon, the predicted glucose trajectory being generated based on the current glucose value and the insulin delivery pattern;
   comparing the desired glucose trajectory against the predicted glucose trajectory;
   responsive to a difference between the desired glucose trajectory and the predicted glucose trajectory being no larger than a predetermined threshold, selecting the predicted glucose trajectory, wherein the difference is determined based on a cost function;
   determining the insulin delivery pattern used to generate the predicted glucose trajectory; and
   causing insulin delivery by the insulin delivery device in accordance with the determined insulin delivery pattern.

2. The processor-implemented method of claim 1, wherein generating the predicted glucose trajectory comprises using a metabolic model to replicate insulin and glucose kinetics and dynamics of the user.

3. The processor-implemented method of claim 1, wherein the cost function comprises an error function describing a difference between the desired glucose trajectory and the predicted glucose trajectory.

4. The processor-implemented method of claim 3, wherein the cost function further comprises a penalty function that provides a check against sudden changes in insulin delivery.

5. The processor-implemented method of claim 3, wherein the cost function further comprises a penalty function that provides a check against large increases in a total amount of insulin delivered.

6. The processor-implemented method of claim 1, wherein the current glucose value is obtained from a glucose sensor system configured to measure glucose values of the user at periodic intervals.

7. The processor-implemented method of claim 6, wherein the method is repeated at regular intervals corresponding to the periodic intervals.

8. A system comprising:
   one or more processors; and
   one or more processor-readable storage media storing instructions which, when executed by the one or more processors, cause performance of a method comprising:
   obtaining a current glucose value for a user of an insulin delivery device;
   generating a desired glucose trajectory that approaches a desired steady state setpoint from the current glucose value over a prediction horizon;

generating an insulin delivery pattern corresponding to an amount of insulin to be delivered to the user over a control horizon;
generating a predicted glucose trajectory over the control horizon, the predicted glucose trajectory being generated based on the current glucose value and the insulin delivery pattern;
comparing the desired glucose trajectory against the predicted glucose trajectory;
responsive to a difference between the desired glucose trajectory and the predicted glucose trajectory being no larger than a predetermined threshold, selecting the predicted glucose trajectory, wherein the difference is determined based on a cost function;
determining the insulin delivery pattern used to generate the predicted glucose trajectory; and
causing insulin delivery by the insulin delivery device in accordance with the determined insulin delivery pattern.

9. The system of claim 8, wherein generating the predicted glucose trajectory comprises using a metabolic model to replicate insulin and glucose kinetics and dynamics of the user.

10. The system of claim 8, wherein the cost function comprises an error function describing a difference between the desired glucose trajectory and the predicted glucose trajectory.

11. The system of claim 10, wherein the cost function further comprises a penalty function that provides a check against sudden changes in insulin delivery.

12. The system of claim 10, wherein the cost function further comprises a penalty function that provides a check against large increases in a total amount of insulin delivered.

13. The system of claim 8, wherein the current glucose value is obtained from a glucose sensor system configured to measure glucose values of the user at periodic intervals.

14. The system of claim 13, wherein the method is repeated at regular intervals corresponding to the periodic intervals.

15. One or more non-transitory processor-readable storage media storing instructions which, when executed by one or more processors, cause performance of a method comprising:
obtaining a current glucose value for a user of an insulin delivery device;
generating a desired glucose trajectory that approaches a desired steady state setpoint from the current glucose value over a prediction horizon;
generating an insulin delivery pattern corresponding to an amount of insulin to be delivered to the user over a control horizon;
generating a predicted glucose trajectory over the control horizon, the predicted glucose trajectory being generated based on the current glucose value and the insulin delivery pattern;
comparing the desired glucose trajectory against the predicted glucose trajectory;
responsive to a difference between the desired glucose trajectory and the predicted glucose trajectory being no larger than a predetermined threshold, selecting the predicted glucose trajectory, wherein the difference is determined based on a cost function;
determining the insulin delivery pattern used to generate the predicted glucose trajectory; and
causing insulin delivery by the insulin delivery device in accordance with the determined insulin delivery pattern.

16. The one or more non-transitory processor-readable storage media of claim 15, wherein generating the predicted glucose trajectory comprises using a metabolic model to replicate insulin and glucose kinetics and dynamics of the user.

17. The one or more non-transitory processor-readable storage media of claim 15, wherein the cost function comprises an error function describing a difference between the desired glucose trajectory and the predicted glucose trajectory.

18. The one or more non-transitory processor-readable storage media of claim 17, wherein the cost function further comprises a penalty function that provides a check against sudden changes in insulin delivery.

19. The one or more non-transitory processor-readable storage media of claim 17, wherein the cost function further comprises a penalty function that provides a check against large increases in a total amount of insulin delivered.

20. The one or more non-transitory processor-readable storage media of claim 15, wherein the current glucose value is obtained from a glucose sensor system configured to measure glucose values of the user at periodic intervals, and wherein the method is repeated at regular intervals corresponding to the periodic intervals.

* * * * *